(12) United States Patent
Obermiller et al.

(10) Patent No.: US 9,492,149 B2
(45) Date of Patent: Nov. 15, 2016

(54) FISTULA GRAFTS AND RELATED METHODS AND SYSTEMS USEFUL FOR TREATING GASTROINTESTINAL AND OTHER FISTULAE

(75) Inventors: F. Joseph Obermiller, West Lafayette, IN (US); Steve Chen, Westfield, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 1053 days.

(21) Appl. No.: 12/269,548

(22) Filed: Nov. 12, 2008

(65) Prior Publication Data

US 2009/0125119 A1    May 14, 2009

Related U.S. Application Data

(60) Provisional application No. 60/987,768, filed on Nov. 13, 2007, provisional application No. 60/988,041, filed on Nov. 14, 2007.

(51) Int. Cl.
*A61B 17/00* (2006.01)

(52) U.S. Cl.
CPC ............ *A61B 17/0057* (2013.01); *A61B 90/39* (2016.02); *A61B 2017/00477* (2013.01); *A61B 2017/00641* (2013.01); *A61B 2090/0811* (2016.02)

(58) Field of Classification Search
CPC .............. A61B 17/0057; A61B 19/54; A61B 2019/4857; A61B 2017/00641; A61B 2017/0061; A61B 2017/00628; A61B 2017/592; A61B 2017/00597
USPC ................ 606/139, 151, 157, 158, 213, 215
See application file for complete search history.

(56) References Cited

U.S. PATENT DOCUMENTS 3,874,388 A * 4/1975 King et al. ..................... 606/232
4,981,465 A    1/1991 Ballan
(Continued)

FOREIGN PATENT DOCUMENTS

EP    1570788    9/2005
EP    1671591    6/2006
(Continued)

OTHER PUBLICATIONS

Himpson, Rebecca C., et al. "Histological evidence for enhanced anal fistula repair using autologous fibroblasts in a dermal collagen matrix". Comparative Clinical Pathology, Apr. 2006, vol. 16, No. 1.
(Continued)

*Primary Examiner* — Alexander Orkin
(74) *Attorney, Agent, or Firm* — Woodard, Emhardt, Moriaty, McNett & Henry LLP

(57) ABSTRACT

Described are medical products, systems, and methods useful for treating fistulae, particularly enterocutaneous fistulae. Certain inventive products are configured to have portions residing in and around a primary fistula opening in a wall of the alimentary canal. One product includes a graft body which is configured to block at least the primary opening. The graft body includes a capping member connected to an elongate plug member. The capping member is configured to contact portions of the alimentary canal wall adjacent to the primary opening, with the elongate plug member extending into at least a portion of the fistula. A product of this sort may be particularly adapted to allow a portion of the capping member to be positioned alongside an exterior, lateral surface of the plug member, e.g., when placed in a delivery device lumen. Such a capping member may be hingedly or non-hingedly coupled to the elongate plug member.

19 Claims, 6 Drawing Sheets

(56) References Cited

U.S. PATENT DOCUMENTS

| | | | | |
|---|---|---|---|---|
| 5,061,274 | A | * | 10/1991 | Kensey .................. 606/213 |
| 5,334,216 | A | | 8/1994 | Vidal |
| 5,334,217 | A | | 8/1994 | Das |
| 5,374,261 | A | | 12/1994 | Yoon |
| RE34,866 | E | | 2/1995 | Kensey |
| 5,451,235 | A | | 9/1995 | Lock |
| 5,584,827 | A | | 12/1996 | Korteweg |
| 5,620,461 | A | | 4/1997 | Muijs Van De Moer |
| 5,752,974 | A | | 5/1998 | Rhee |
| 5,861,003 | A | * | 1/1999 | Latson et al. .................. 606/213 |
| 5,879,366 | A | * | 3/1999 | Shaw et al. ................... 606/213 |
| 5,904,703 | A | * | 5/1999 | Gilson ........................ 606/213 |
| 6,090,996 | A | | 7/2000 | Li |
| 6,174,322 | B1 | * | 1/2001 | Schneidt ..................... 606/213 |
| 6,315,787 | B1 | | 11/2001 | Tsugita |
| 6,569,081 | B1 | | 5/2003 | Nielsen |
| 6,712,836 | B1 | * | 3/2004 | Berg et al. ................... 606/213 |
| 2002/0019648 | A1 | * | 2/2002 | Akerfeldt et al. ............ 606/213 |
| 2002/0026208 | A1 | | 2/2002 | Roe |
| 2003/0028213 | A1 | * | 2/2003 | Thill et al. .................... 606/200 |
| 2004/0133236 | A1 | * | 7/2004 | Chanduszko ................ 606/213 |
| 2004/0158185 | A1 | | 8/2004 | Moran et al. |
| 2004/0176798 | A1 | | 9/2004 | Epstein et al. |
| 2004/0215231 | A1 | * | 10/2004 | Fortune et al. ............... 606/213 |
| 2005/0013844 | A1 | | 1/2005 | Hadlock et al. |
| 2005/0049626 | A1 | | 3/2005 | Burgard |
| 2005/0155612 | A1 | * | 7/2005 | Matsuura et al. ............ 128/887 |
| 2005/0182495 | A1 | | 8/2005 | Perrone |
| 2005/0234509 | A1 | * | 10/2005 | Widomski et al. ........... 606/213 |
| 2006/0015142 | A1 | | 1/2006 | Malazgirt |
| 2006/0122646 | A1 | | 6/2006 | Corcoran et al. |
| 2007/0073337 | A1 | * | 3/2007 | Abbott et al. ................ 606/213 |
| 2007/0118176 | A1 | | 5/2007 | Opolski et al. |
| 2007/0123934 | A1 | * | 5/2007 | Whisenant et al. .......... 606/213 |
| 2007/0282373 | A1 | * | 12/2007 | Ashby et al. ................. 606/213 |

FOREIGN PATENT DOCUMENTS

| | | |
|---|---|---|
| RU | 1673130 | 8/2001 |
| RU | 2180529 | 3/2002 |
| SU | 1690737 | 11/1991 |
| WO | WO 93/07813 | 4/1993 |
| WO | WO 00/19912 | 4/2000 |
| WO | WO 00/72759 | 12/2000 |
| WO | WO 2004/102627 | 11/2004 |
| WO | WO 2005/020823 | 3/2005 |
| WO | WO 2007/002260 | 1/2007 |
| WO | WO 2007/064819 | 6/2007 |
| WO | WO 2007/090150 A2 | 8/2007 |
| WO | WO 2007/149989 A2 | 12/2007 |

OTHER PUBLICATIONS

Khairy, G. E. A., et al. "Percutaneous obliteration of duodenal fistula". J.R. Coll. Surg. Edinb., 45, Oct. 2000, 342-344.

Lisle, David A., et al. "Percutaneous Gelfoam Embolization of Chronic Enterocutaneous Fistulas: Report of Three Cases". Diseases of the Colon & Rectum, vol. 50, No. 2, Dec. 2006.

Moore, Robert D., et al. "Rectovaginal Fistula Repair Using a Porcine Dermal Graft". Obstetrics & Gynecology, 2004, 104, 1165-1167.

Schwesinger, Wayne H., "Management of Persistent Fistula After Gastrectomy" on-line question (www.medscape.com), posted on May 14, 2002.

Shah, A. M., et al. "Bronchoscopic closure of bronchopleural fistula using gelfoam" abstract. Journal of Association of Physicians of India, 2004, vol. 52, No. JUIN, pp. 508-509.

Shaker MA, Hindy AM, Mounir RM, Geaisa KM. Egypt Dent J. Jul. 1995; 41(3): 1237-42.

Sheiman, Robert G., et al. "Percutaneous Treatment of a Pancreatic Fistula after Pancreaticoduodenectomy". J Vasc Intery Radiol, 2001, vol. 12, No. 4, pp. 524-526.

Shelton, Andrew A., et al. Transperineal Repair of Persistent Rectovaginal Fistulas Using an Acellular Cadaveric Dermal Grant (AlloDerm®). Diseases of the Colon & Rectum, Sep. 2006, vol. 49, No. 9.

Wilson Gunn on behalf of unnamed party, Letter to the European Patent Office, Jan. 30, 2007, pp. 1-4.

\* cited by examiner

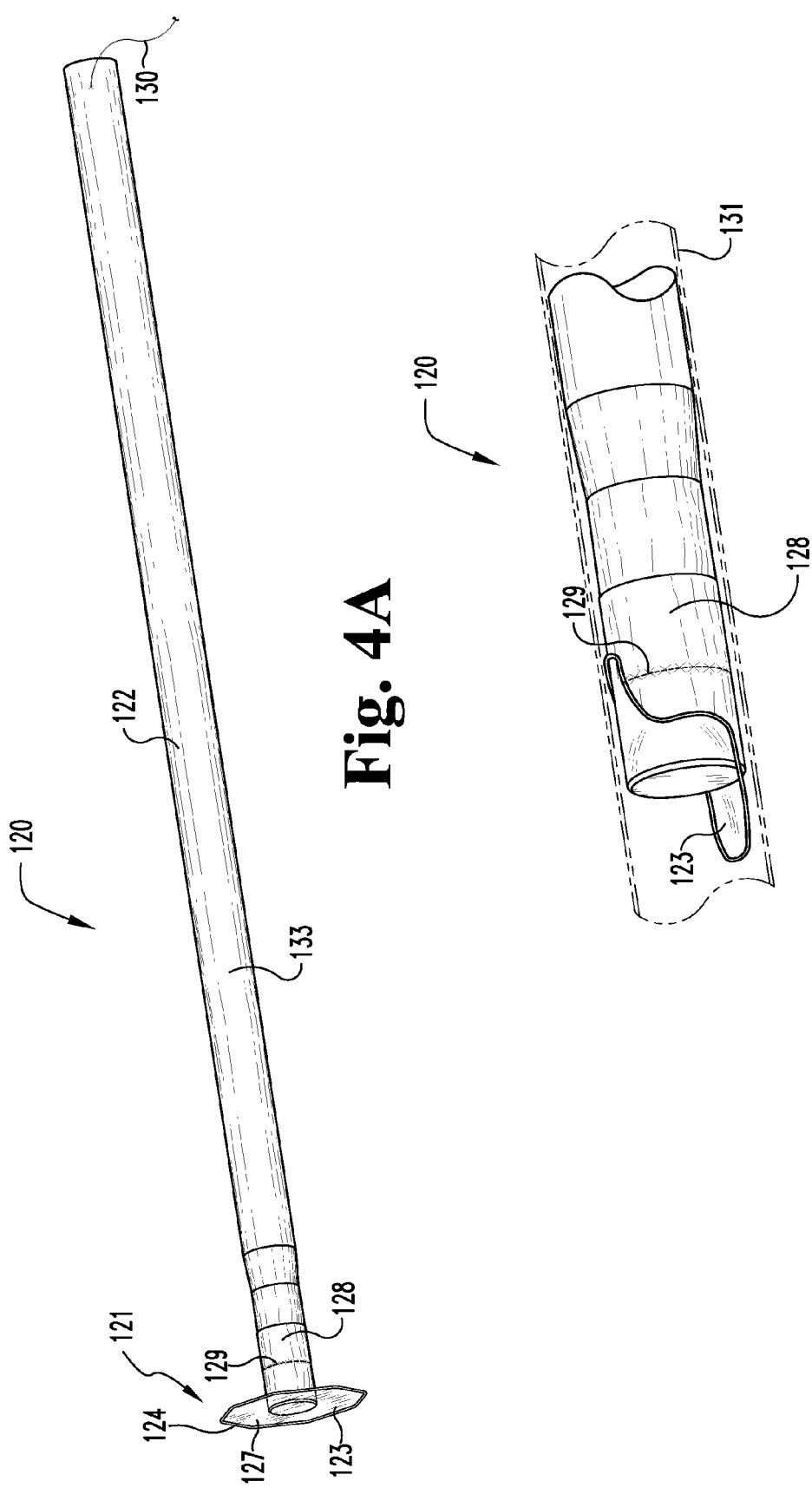

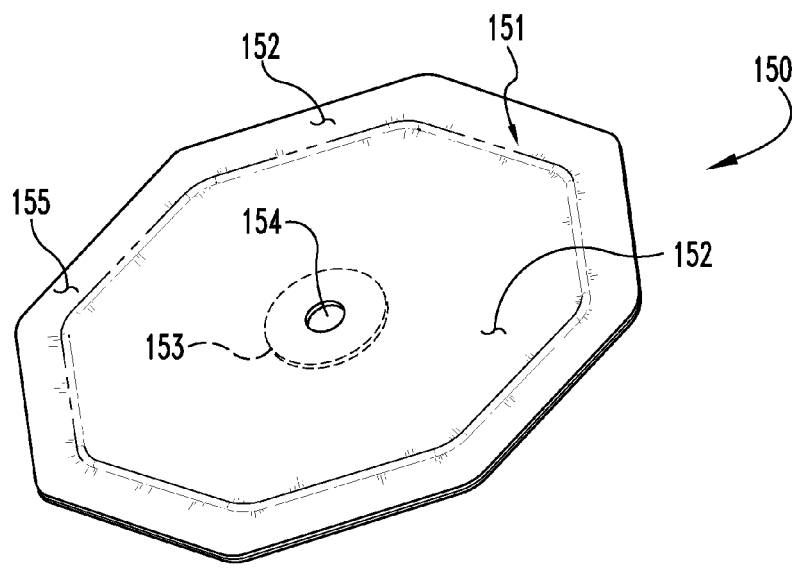
Fig. 5
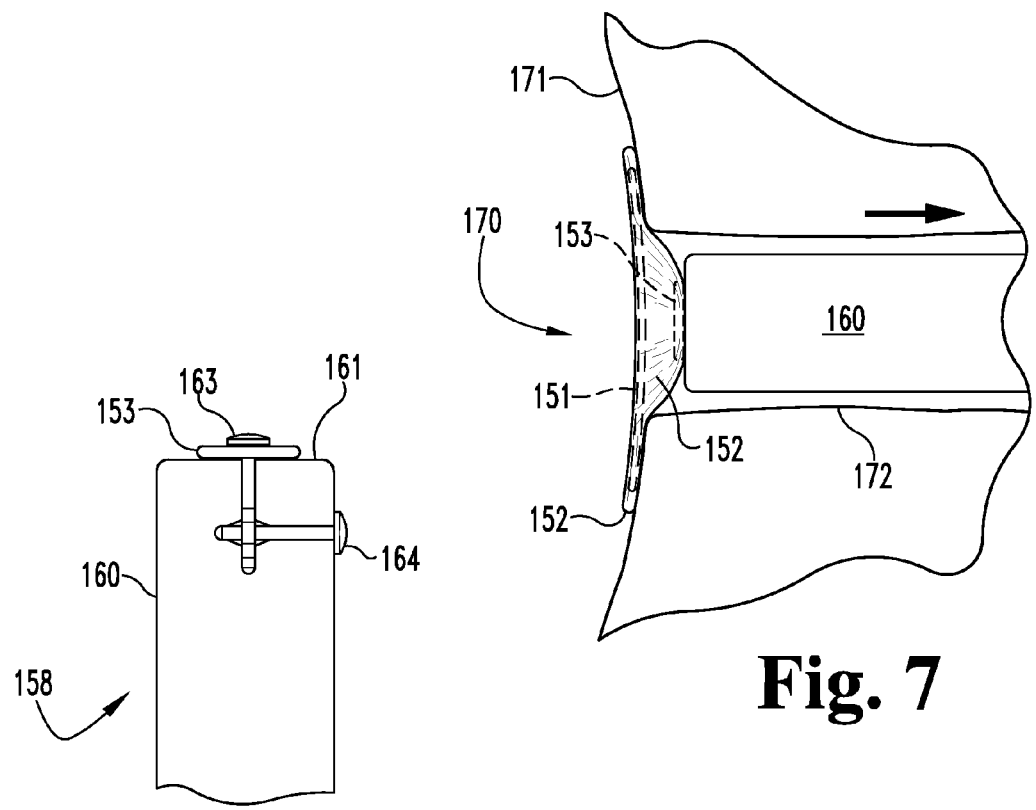
Fig. 6
Fig. 7

FISTULA GRAFTS AND RELATED METHODS AND SYSTEMS USEFUL FOR TREATING GASTROINTESTINAL AND OTHER FISTULAE

REFERENCE TO RELATED APPLICATIONS

The present application claims the benefit of U.S. Provisional Patent Application Ser. No. 60/987,768 filed Nov. 13, 2007 and U.S. Provisional Patent Application Ser. No. 60/988,041 filed Nov. 14, 2007, both entitled FISTULA GRAFTS AND RELATED METHODS AND SYSTEMS USEFUL FOR TREATING GASTROINTESTINAL AND OTHER FISTULAE, each of which is incorporated herein by reference in its entirety.

BACKGROUND

The present invention relates generally to medical technology and in particular aspects to devices and methods for treating fistulae and other passageways in the body.

As further background, there exist a variety of passages and other open spaces in the body which can be plugged, filled, blocked, etc. to provide benefit to the patient. For example, it may be desirable to occlude a lumen or other open space in the vasculature (e.g., a blood vessel such as a vein or artery). In some instances, a device is deployed within the venous system, e.g., within the greater and/or lesser saphenous vein, to treat complications, such as a varicose vein conditions.

As well, it may be desirable to plug or otherwise fill a fistula. A variety of fistulae can occur in humans. These fistulae can occur for a variety of reasons, such as but not limited to, as a congenital defect, as a result of inflammatory bowel disease, such as Crohn's disease, irradiation, trauma, such as childbirth, or as a side effect from a surgical procedure. Further, several different types of fistulae can occur, for example, urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, recto-urethral fistulae, or recto-prostatic fistulae.

The path which fistulae take, and their complexity, can vary. A fistula may take a take a "straight line" path from a primary opening to a secondary opening, known as a simple fistula. Alternatively, a fistula may comprise multiple tracts ramifying from a primary opening and have multiple secondary openings. This is known as a complex fistula.

Anorectal fistulae can result from infection in the anal glands, which are located around the circumference of the distal anal canal that forms the anatomic 35 landmark known as the dentate line. Approximately 20-40 such glands are found in humans. Infection in an anal gland can result in an abscess. This abscess then can track through soft tissues (e.g., through or around the sphincter muscles) into the perianal skin, where it drains either spontaneously or surgically. The resulting void through soft tissue is known as a fistula. The internal or inner opening of the fistula, usually located at or near the dentate line, is known as the primary opening. Any external or outer openings, which are usually located in the perianal skin, are known as secondary openings.

One technique for treating a perianal fistula is to make an incision adjacent the anus until the incision contacts the fistula and then excise the fistula from the anal 10 tissue. This surgical procedure tends to sever the fibers of the anal sphincter, and may cause incontinence. Other surgical treatment of fistulae involve passing a fistula probe through the tract of the fistula in a blind manner, using primarily only tactile sensation and experience to guide to probe. Having passed the probe through the fistula tract, the overlying tissue is surgically divided. This is known as a fistulotomy. Since a variable amount of sphincter muscle is divided during the procedure, fistulotomy also may result in impaired sphincter control, and even frank incontinence.

A gastrointestinal fistula is an abnormal passage that leaks contents of the stomach or the intestine (small or large bowel) to other organs, usually other parts of the intestine or the skin. For example, gastrojejunocolic fistulae include both enterocutaneous fistulae (those occurring between the skin surface and the intestine, namely the duodenum, the jejunum, and the ileum) and gastric fistulae (those occurring between the stomach and skin surface). Another type of fistula occurring in the gastrointestinal tract is an enteroenteral fistula, which refers to a fistula occurring between two parts of the intestine. Gastrointestinal fistulae can result in malnutrition and dehydration depending on their location in the gastrointestinal tract. They can also be a source of skin problems and infection. The majority of these types of fistulae are the result of surgery (e.g., bowel surgery), although sometimes they can develop spontaneously or from trauma, especially penetrating traumas such as stab wounds or gunshot wounds. Inflammatory processes, such as infection or inflammatory bowel disease (Crohn's disease), may also cause gastrointestinal fistulae. In fact, Crohn's disease is the most common primary bowel disease leading to enterocutaneous fistulae, and surgical treatment may be difficult because additional enterocutaneous fistulae develop in many of these patients postoperatively.

Treatment options for gastrointestinal fistulae vary. Depending on the clinical situation, patients may require IV nutrition and a period of time without food to allow the fistula time to close on its own. Indeed, nonsurgical therapy may allow spontaneous closure of the fistula, although this can be expected less than 30% of the time according to one estimate. A variable amount of time to allow spontaneous closure of fistulae has been recommended, ranging from 30 days to 6 to 8 weeks. During this preoperative preparation, external control of the fistula drainage prevents skin disruption and provides guidelines for fluid and electrolyte replacement. In some cases, surgery is necessary to remove the segment of intestine involved in a non-healing fistula.

When surgery is deemed necessary, one operation for fistula closure is resection of the fistula-bearing segment and primary end-to-end anastomosis. The anastomosis may be reinforced by greater omentum or a serosal patch from adjacent small bowel. Still other methods for treating fistulae involve injecting sclerosant or sealant (e.g., collagen or fibrin glue) into the tract of the fistula to block the fistula. Closure of a fistula using a sealant is typically performed as a two-stage procedure, including a first-stage seton placement and injection of the fibrin glue several weeks later. This allows residual infection to resolve and to allow the fistula tract to "mature" prior to injecting a sealant. If sealant or sclerosant were injected as a one-stage procedure, into an "unprepared" or infected fistula, this may cause a flare-up of the infection and even further abscess formation.

There remain needs for improved and/or alternative devices, systems and methods for treating fistulae and other sites in the body. The present invention is addressed to those needs.

SUMMARY

The present invention provides, in certain aspects, unique medical products for treating fistulae having at least a primary opening in the alimentary canal and a fistula tract. Certain embodiments of the invention relate to fistula grafts which are configured to have portions residing in and around a primary fistula opening, such as a gastrointestinal fistula primary opening. For example, some inventive fistula grafts include a biocompatible graft body which is configured to block at least the primary fistula opening, wherein the graft body comprises a capping member and an elongate plug member, which extends from the capping member. The capping member is configured to contact portions of the alimentary canal wall adjacent to the primary opening, and the elongate plug member is configured to extend into at least a portion of the fistula tract. The capping member and the elongate plug member are formed separately and then coupled to one another (e.g., hingedly coupled with a suture) or otherwise suitably united, or alternatively, the two may be formed as a single unit for example, from a single piece of material or other object. In this regard, each of the two members can exhibit any suitable size, shape, and configuration, and may be formed with one or more of a variety of suitable biocompatible materials. In some forms, the graft body is configured to seal off or substantially seal off the primary fistula opening when suitably deployed. The capping member and/or the elongate plug member, in certain aspects, comprise an expandable element, for example, an expandable material such as a compressed sponge material and/or an expandable device such as a resilient wire frame. In preferred aspects, the capping member and/or the elongate plug member comprise a remodelable, angiogenic material, for example, a remodelable extracellular matrix material such as submucosa. Further, the medical graft product, in some forms, can include a suture in association with the graft body. This suture can be used, for example, to draw the product into the fistula primary opening and/or to secure the product to soft tissues at or near a secondary opening in the fistula.

In one particular embodiment, the invention provides a method for treating a fistula having a primary opening in a wall of the alimentary canal and a fistula tract. This method comprises (i) providing a medical graft product including a biocompatible graft body that is configured to block at least the primary fistula opening, wherein the graft body includes a capping member and an elongate plug member extending from the capping member; said capping member being hingedly coupled to said elongate plug member and (ii) implanting the medical graft product within a patient so that the capping member contacts portions of the alimentary canal wall adjacent to the primary opening, and the elongate plug member extends into at least a portion of the fistula tract. In certain aspects, a suitably configured medical graft product is implanted so as to seal off or substantially seal off the primary opening. Further, the medical graft product may include an anchoring adaptation useful for maintaining the capping member in contact with portions of the alimentary canal wall adjacent to the primary opening. Suitable anchoring adaptations include but are not limited to adhesives (e.g., dried, reversible adhesives), barbs, hooks, sutures, and the like.

In another embodiment, the present invention provides a medical graft product useful for treating a fistula having a primary opening in a wall of the alimentary canal and a fistula tract. This medical graft product includes a biocompatible graft body configured to block at least the primary opening of the fistula. The graft body is comprised of a capping member and an elongate plug member. The plug member has a proximal and distal end, with a lumen extending therethrough. The capping member extends from the distal end of the elongate plug member, and is configured to contact portions of the alimentary canal wall adjacent to the primary opening. The elongate plug member is configured to extend into at least a portion of the fistula tract, and includes a plurality of passages. The longitudinal axis of each passage runs through the plug member lumen to allow communication between opposing sides of the exterior surface of the elongate plug member.

Another aspect of the present invention provides a graft product for treating a fistula, which is comprised of a graft body configured to reside in a tract of the fistula, and a capping member configured to contact tissues adjacent an opening of the fistula. The capping member is connected to an end region of the graft body, and includes a portion positionable along an exterior lateral surface of the graft body.

In yet another aspect, the invention provides a medical graft product that is comprised of a capping member, and an elongate graft body extending from the capping member. The capping member includes a portion positionable over an exterior lateral surface of the elongate graft body. This portion is conformable to the exterior lateral surface of the elongate graft body.

The present invention provides, in another embodiment, an apparatus for treating a fistula having at least an opening in a bodily structure wall and a fistula tract extending from the opening. This apparatus comprises a delivery device having a lumen communicating with a distal end opening, wherein the delivery device is configured for passage through the fistula tract and the opening. The apparatus also comprises a medical graft device removably positioned in the delivery device lumen. The medical graft device is comprised of a biocompatible graft body, and includes a capping member and an elongate plug member. The capping member is configurable to a first condition permitting at least part of the capping member to be positioned along an exterior lateral surface of the elongate plug member when in the delivery device lumen. The elongate plug member extends from the capping member, and is effective to fill at least a portion of the fistula tract.

Another aspect of the present invention provides a method for implanting a medical device in a patient. In one method step, an implantable medical device is provided. This medical device comprises a device body, a first imageable component and a second imageable component. The device body includes a deformable anchoring component that is deformable from a first condition to a second condition. In another method step, the medical device is delivered to an implantation site in the patient. In another step, the anchoring component is deformed from the first condition to the second condition, wherein the first imageable component changes position relative to the second imageable component. In another step, the change in position of the first imageable component relative to the second imageable component is visualized.

In another embodiment, the present invention provides an implantable medical device. This medical device comprises a device body, a first imageable component and a second imageable component. The device body includes a deformable anchoring component that is deformable from a first condition to a second condition. The first imageable component and the second imageable component are arranged such that upon deformation of the anchoring component from the first condition to the second condition, the position of the first imageable component relative to the second imageable component changes.

In another illustrative embodiment, the invention provides a medical graft device useful for treating a fistula having at least a primary opening in a bodily structure wall and a fistula tract extending from the primary opening. This medical graft device comprises a biocompatible graft body that includes a capping member and an elongate plug member. The elongate plug member extends from the capping member, and is configured to fill at least a portion of the fistula tract. This medical graft device also includes a retaining system for retaining the capping member in association with the plug member. The retaining system includes a first pin or other retaining member and a second pin or other retaining member. The first pin is configured for insertion through an aperture in the capping member and into a generally longitudinal, first passage in the plug member. The second pin is configured for insertion into a generally lateral, second passage in the plug member. The first pin and the second pin are configured to engage one another in the plug member for maintaining the first pin and the second pin in the plug member.

An additional embodiment of the present invention provides a medical graft device useful for treating a fistula having at least a primary opening in a bodily structure wall and a fistula tract extending from the primary opening. This medical graft device comprises a biocompatible graft body including a capping member and an elongate member that extends from the capping member. The capping member includes a peripheral support frame and a radiopaque component that is positioned to the interior of the support frame. The elongate member is configured to extend through the fistula tract when the graft device is implanted.

In another aspect, the invention provides a method for treating a fistula having at least a primary opening in a bodily structure wall and a fistula tract extending from the primary opening. One step in this method includes providing a medical graft device that includes a biocompatible graft body. This graft body includes a capping member and an actuating member that extends from the capping member. The capping member is deformable to a deformed condition that includes an externalized radiopaque portion and an internalized radiopaque portion. The actuating member is configured to extend through the fistula tract when the graft device is implanted, and is actuatable to convert the capping member to the deformed condition. In another method step, the medical graft device is positioned in a patient such that the capping member contacts portions of the bodily structure wall adjacent to the primary opening, and the actuating member extends into at least a portion of the fistula tract. In another method step, the actuating member is pulled in a direction generally away from the primary opening so as to convert the capping member to the deformed condition. In this deformed condition, the externalized radiopaque portion resides externally of the fistula tract, and the internalized radiopaque portion resides within the fistula tract and is spaced a distance from the externalized radiopaque portion.

In yet another embodiment, the present invention provides a medical graft device useful for treating a fistula having at least a primary opening in a bodily structure wall and a fistula tract extending from the primary opening. This medical graft device comprises a biocompatible graft body that includes a capping member and an actuating member extending from the capping member. The capping member is deformable to a deformed condition that including an externalized radiopaque portion and an internalized radiopaque portion. The externalized radiopaque portion is configured to reside externally of the fistula tract when the graft device is implanted and the capping member is deformed. The internalized radiopaque portion is configured to reside within the fistula tract and be spaced a distance from the externalized radiopaque portion when the graft device is implanted and the capping member is deformed. The actuating member is configured to extend through the fistula tract when the graft device is implanted, and is actuatable to convert the capping member to the deformed condition.

Other objects, embodiments, forms, features, advantages, aspects, and benefits of the present invention shall become apparent from the detailed description and drawings included herein.

BRIEF DESCRIPTION OF THE DRAWINGS

FIG. 4A is a perspective view of a medical graft device of the invention.

FIG. 4B is a partial, perspective view of the medical graft device of FIG. 4A positioned in a delivery device lumen.

FIG. 5 provides a perspective view of a capping member of the present invention.

FIG. 6 provides a partial, side view of granting device according to one embodiment of the present invention.

FIG. 7 shows the grafting device of FIG. 6 implanted within a patient.

DETAILED DESCRIPTION

Figure 1A:
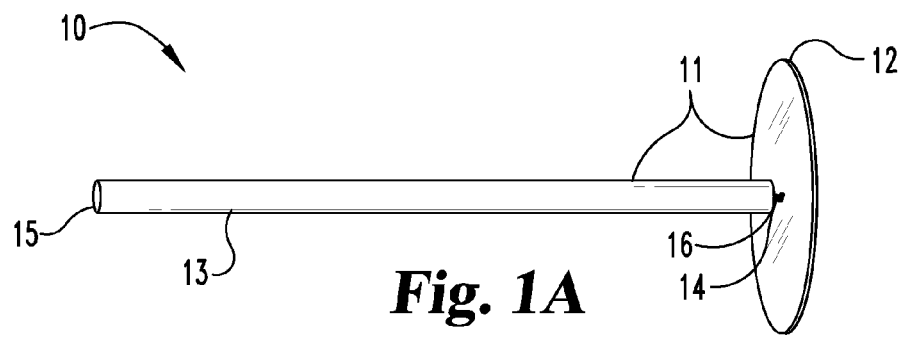
FIG. 1A is a perspective view of an illustrative medical graft product in its original configuration including an elongate plug member and a capping member hingedly coupled thereto.

As disclosed above, in certain aspects, the present invention provides unique medical graft products and methods useful for treating fistulae having at least a fistula tract and a primary opening in the alimentary canal or other similar voids in bodily tissues. For example, some inventive graft products include a biocompatible graft body which is configured to block at least the primary fistula opening, wherein the graft body includes a capping member and an elongate plug member extending from the capping member. The capping member is configured to contact portions of the alimentary canal wall adjacent to the primary opening, and the elongate plug member is configured to extend into at least a portion of the fistula tract. The elongate plug member and the capping member are preferably formed separately and then coupled to one another by a coupling element. The biocompatible graft body preferably comprises a remodelable material, for example, a remodelable extracellular matrix material such as submucosa. The invention also provides methods utilizing such graft products and medical products that include such graft products enclosed within sterile packaging.

Graft materials useful in the medical graft products of the present invention can include any suitable biocompatible material. Generally, the graft materials may include a remodelable and/or resorbable material, such as a resorbable synthetic material or a naturally derived resorbable or remodelable material. Additionally, graft materials can include any other suitable naturally derived or any other suitable nonresorbable synthetic material, or any combination of any of the above such biocompatible materials. Such biocompatible materials that are at least bioresorbable will provide advantage in certain embodiments of the invention, with materials that are bioremodelable or otherwise tissue inductive so as to promote cellular invasion and ingrowth providing particular advantage. Illustratively, remodelable materials may be used in this context to promote cellular growth within the graft materials to promote healing and closure of at least the primary opening of a fistula.

Suitable materials for use in the invention can be provided by collagenous extracellular matrix (ECM) materials, including but not limited to those possessing biotropic or remodelable properties, including in certain forms angiogenic collagenous extracellular matrix materials. For example, suitable collagenous materials include ECM materials such as those comprising submucosa, renal capsule membrane, dermal collagen (including processed dermal collagen from human cadavers, which can be used as allograft in humans), dura mater, pericardium, facia lata, serosa, peritoneum, or basement membrane layers, including liver basement membrane. Suitable submucosa materials for these purposes include, for instance, intestinal submucosa, including small intestinal submucosa, stomach submucosa, urinary bladder submucosa, and uterine submucosa. Some preferred medical graft products of the invention will include submucosa, such as submucosa derived from a warm-blooded vertebrate. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa (SIS), more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information concerning submucosa useful in certain embodiments of the present invention, and its isolation and treatment, reference can be made, for example, to U.S. Pat. Nos. 4,902,508, 5,554,389, 5,993,844, 6,206,931, and 6,099,567.

Submucosa-containing or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

As prepared and used, the submucosa material or any other ECM material may optionally retain and/or otherwise include growth factors or other bioactive components native to the source tissue. For example, the submucosa or other ECM material may retain one or more growth factors such as basic fibroblast growth factor (FGF-2), transforming growth factor beta (TGF-beta), epidermal growth factor (EGF), cartilage derived growth factor (CDGF) and/or platelet derived growth factor (PDGF). As well, submucosa or other ECM material used in certain embodiments of the invention may retain or include other biological materials such as but not limited to proteins, glycoproteins, proteoglycans, and glycosaminoglycans. For example, ECM materials may include heparin, heparin sulfate, hyaluronic acid, fibronectin, cytokines and the like. Thus, generally speaking, the submucosa or other ECM material may retain or otherwise include a bioactive component that induces, directly or indirectly, a cellular response such as a change in cell morphology, proliferation, growth, protein or gene expression.

Further, in addition or as an alternative to the inclusion of such native bioactive components, non-native bioactive components such as those synthetically produced by recombinant technology or other methods, may be incorporated into the submucosa or other ECM material. These non-native bioactive components may be naturally-derived or recombinantly produced proteins that correspond to those natively occurring in the ECM material, but perhaps of a different species (e.g. human proteins applied to collagenous ECMs from other animals, such as pigs). The normative bioactive components may also be drug substances. Illustrative drug substances that may be incorporated into and/or onto the ECM material can include, for example, antibiotics and/or thrombus-promoting substances such as blood clotting factors, e.g. thrombin, fibrinogen, and the like. These substances may be applied to the ECM material as a pre-manufactured step, immediately prior to the procedure (e.g. by soaking the material in a solution containing a suitable antibiotic such as cefazolin), or during or after engraftment of the ECM material within the patient.

Medical graft products of the invention can include xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substance incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

Submucosa or other ECM material used in certain embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in certain embodiments of the invention is preferably disinfected with an oxidizing agent, particularly a peracid, such as peracetic acid. These and additional properties of submucosa or other ECM materials taught in U.S. Pat. No. 6,206,931 may be characteristic of the submucosa used in certain embodiments of the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

ECM materials used in the invention may be free or essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

Turning now to a discussion of drying techniques that can be useful in certain embodiments of the invention, drying by evaporation, or air drying, generally comprises drying a partially or completely hydrated remodelable material by allowing the hydrant to evaporate from the material. Evaporative cooling can be enhanced in a number of ways, such as by placing the material in a vacuum, by blowing air over the material, by increasing the temperature of the material, by applying a blotting material during evaporation, or by any other suitable means or any suitable combination thereof. The amount of void space or open matrix structure within an ECM material that has been dried by evaporation is typically more diminished than, for example, an ECM material dried by lyophilization as described below.

A suitable lyophilization process can include providing an ECM material that contains a sufficient amount of hydrant such that the voids in the material matrix are filled with the hydrant. The hydrant can comprise any suitable hydrant known in the art, such as purified water or sterile saline, or any suitable combination thereof. Illustratively, the hydrated material can be placed in a freezer until the material and hydrant are substantially in a frozen or solid state. Thereafter, the frozen material and hydrant can be placed in a vacuum chamber and a vacuum initiated. Once at a sufficient vacuum, as is known in the art, the frozen hydrant will sublime from the material, thereby resulting in a dry remodelable material.

In alternative embodiments, a hydrated ECM material can be lyophilized without a separately performed pre-freezing step. In these embodiments, a strong vacuum can be applied to the hydrated material to result in rapid evaporative cooling which freezes the hydrant within the ECM material. Thereafter, the frozen hydrant can sublime from the material thereby drying the ECM material. Desirably, an ECM material that is dried via lyophilization maintains a substantial amount of the void space, or open matrix structure, that is characteristic of the harvested ECM material.

Drying by vacuum pressing generally comprises compressing a fully or partially hydrated remodelable material while the material is subject to a vacuum. One suitable method of vacuum pressing comprises placing a remodelable material in a vacuum chamber having collapsible walls. As the vacuum is established, the walls collapse onto and compress the material until it is dry. Similar to evaporative drying, when a remodelable material is dried in a vacuum press, more of the material's open matrix structure is diminished or reduced than if the material was dried by lyophilization.

In certain aspects, the invention provides medical products including a multilaminate material. Such multilaminate materials can include a plurality of ECM material layers bonded together, a plurality of non-ECM materials bonded together, or a combination of one or more ECM material layers and one or more non-ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. As well, bonding can be achieved or facilitated between ECM material layers using chemical cross-linking agents such as those described above. A combination of one or more of these with dehydration-induced bonding may also be used to bond ECM material layers to one another.

A variety of dehydration-induced bonding methods can be used to fuse together portions of an ECM material. In one preferred embodiment, multiple layers of ECM material are compressed under dehydrating conditions. In this context, the term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressed surfaces. One particularly useful method of dehydration bonding ECM materials is lyophilization.

Another method of dehydration bonding comprises pulling a vacuum on the assembly while simultaneously employing the vacuum to press the assembly together. Again, this method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying and other operations under relatively mild temperature exposure conditions that minimize deleterious effects upon any ECM materials being used, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

In additional embodiments, medical graft products of the invention can be made from ECM's or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct to a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a tract within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1

M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of sponge or foam shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression similar to a non-expanded collagenous material.

Expanded collagenous materials can be used to prepare a wide variety of fistula plug devices. Methods for preparing such plug devices can include contacting an ECM or other collagenous starting material with an alkaline substance in an amount effective to expand the material, casting or otherwise forming the expanded collagenous material into a plug shape (e.g. one of those described herein), and lyophilizing the expanded material to form a dried plug device.

Medical graft products of the invention may include biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

Suitable biocompatible medical products of the invention can also include a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorbable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate. For further information concerning suitable synthetic materials (both biodegradable and nonbiodegradable), useful in certain embodiments of the present invention, reference can be made, for example, to U.S. Utility Patent Application Pub. No. 2005/022848 6 titled, "Implantable Frame with Variable Compliance," filed on Apr. 11, 2005 ("Express Mail" Mailing Label No. EV 327 135 804 US), which claims priority to U.S. Provisional Patent Application titled, "Implantable Frame with Variable Compliance," filed on Apr. 13, 2004. Such synthetic materials can be used to form fistula plug devices as described herein, either alone or in combination with ECM or other collagenous materials herein identified.

Turning now to a discussion of particular medical graft products, systems, and methods of the present invention useful for treating fistulae, illustrative medical graft products of the invention are configured to block at least the primary opening of a fistula, i.e., the primary opening and potentially one or more other segments of a fistula, for example, the fistula tract and/or any secondary openings. In this context, the term "fistula tract" is meant to include, but is not limited to, a void in soft tissues extending from a primary fistula opening, whether blind-ending or leading to one or more secondary fistula openings, for example, to include what are generally described as simple and complex fistulae. Fistula grafts of the invention include a biocompatible graft body including a capping member and an elongate plug member extending from the capping member. The capping member is configured to contact portions of the alimentary canal wall adjacent to the primary opening, and the elongate plug member is configured to extend into at least a portion of the fistula tract. In performing these functions, the capping member and the elongate plug member can exhibit any suitable size and shape and can include any suitable device and/or material, as long as the graft body is able to block at least the primary opening of a fistula.

In some embodiments, the present invention provides fistula graft products that are useful in treating gastrointestinal fistulae. Illustratively, these products can be configured to block at least a fistula opening occurring in an alimentary canal wall, and particularly those occurring in the stomach and intestine. In advantageous embodiments, these products will at least include a capping member and an elongate plug member extending from the capping member, wherein the capping member is configured to contact portions of the alimentary canal wall adjacent to the fistula opening, and the elongate plug member is configured to extend into, and in some cases fill, at least a portion of a gastrointestinal fistula tract. While these products are particularly suited for treating gastrointestinal fistulae, it will be understood that such products may be useful in treating other types of fistulae as well, and in some forms, are useful in filling, blocking or otherwise treating non-fistula openings or passages occurring in the body.

Any capping member present in an inventive product may be constructed along with the elongate plug member to provide a single unitary construct, for example, a single-capped device formed from a single piece of material or other substance. In some embodiments, a particular capping member may be formed separately from and an elongate plug member and then subsequently combined or otherwise retained in association with the plug member, for example, by suturing the two together, applying an adhesive, using mechanical fastener(s), or employing any other suitable means or combination thereof. In one embodiment, an inventive medical graft product comprises an elongate plug member and a capping member, wherein the capping member is formed separately from the plug member and is hingedly coupled to an end of the plug member, e.g., before or during an implantation procedure. In certain aspects, a capping member and an elongate plug member are formed from separate pieces of material, yet are retained in association with one another without the use of another device or material (e.g., sutures, an adhesive, etc.). In such aspects, the elongate plug member and one or more capping members are joined together by having at least one member (or any portion thereof) received around, through, over, etc., at least one other member (or any portion thereof).

In some forms, one or more capping members are each formed separately from an elongate plug member, and then coupled to the plug member with an absorbable device or material. These coupling elements can exhibit any suitable size, shape, and configuration, and in some embodiments, take the form of an adhesive or one or more hooks, fasteners, barbs, straps, suture strands, or combinations thereof. Additionally, such devices and materials can be configured to degrade at varying rates upon being implanted in vivo. In one embodiment, 2-0 vicryl suture material is used to join one or more capping members to an elongate plug member. Illustratively, a coupling element can be adapted to desirably hold one or more capping members in association with a plug member during product handling and implantation, and then upon implantation, to degrade at a desirable rate. In some modes of operation, a capping member and an elongate plug member, at least due in part to degradation of the coupling element, can uncouple or otherwise disengage from one another after a period of time following implantation, allowing the capping member to pass through and out of the body naturally. In certain embodiments, the capping member can be hingedly coupled to the elongate plug member. By "hingedly coupled" is meant that the capping member is not rigidly fixed to the elongate body member and can therefore tilt or swing relative to the elongate body member while still being coupled to it. For example, prior to loading the medical graft product into a deployment device such as a sheath (e.g., Flexor® sheath available from Cook Urological, Inc., 1100 West Morgan Street, P.O. Box 227 Spencer, Ind. 47460) the capping member can be tilted a distance toward an opposing end (i.e., from the distal end towards the proximal end or vice versa) of the elongate body member and rolled over the elongate body member so as to allow for the medical graft product to be positioned into a deployment device. In this respect, the capping member has an implantable configuration wherein the opposite sides of the member are brought in closer proximity to one another so as to be able to fit within the lumen of a delivery device, such as a catheter or sheath. In certain aspects, the distal end of the deployment device can be inserted into a fistula, for example, into a secondary opening, through a fistula tract, and a distance out of the primary opening. Thereafter, the graft body (or at least the capping member) can be delivered from the deployment device, allowing the capping member to expand. Then, the graft body can be pulled back through the fistula tract until the capping member contacts portions of the alimentary canal wall adjacent to the primary opening. The delivery device can then be withdrawn from the fistula through the secondary opening while maintaining the position of the graft body with a pusher rod or any other suitable means, leaving the graft deployed within the fistula and blocking at least the primary fistula opening.

The capping member is configured to contact portions of the alimentary canal wall adjacent to the primary opening. The capping member may include a frame comprising a single piece of superelastic wire or other material having a plurality of sides and bends interconnecting adjacent sides. The bends can be coils, fillets, or other configurations to reduce stress and fatigue. The single piece of wire is preferably joined by an attachment mechanism, such as a piece of cannula and solder, to form a closed circumference frame.

The frame can comprise a metallic material including but not limited to stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). Additionally or alternatively, suitable frames can include material in the form of yarns, fibers, and/or resins, e.g., monofilament yarns, high tenacity polyester, and the like. A frame element can also include other plastic, resin, polymer, woven, and fabric surgical materials, other conventional synthetic surgical materials, such as a shape-memory plastic, and/or combinations of such materials. Further, appropriate ceramics can be used, including, without limitation, hydroxyapatite, alumina and pyrolytic carbon. Such metallic and other materials may be used in forming other expandable and non-expandable graft body components useful in the present invention. A capping member can also include a flexible material covering extending between sides of the frame. Such a covering can be formed with any suitable material such as but not limited to DACRON®, THORALON®, PTFE, collagen, submucosa, or other flexible material, and can be attached to the frame with sutures or other suitable attachment means.

The capping member can be comprised of a frame in the form of a tulip filter. The capping member may also include a flexible material covering attached to the tulip filter frame. Such a covering can be formed with any suitable material such as but not limited to DACRON, PTFE, collagen, submucosa, or other flexible material, and can be attached to the tulip filter with sutures or other suitable means. In certain other aspects, such a covering is not included as part of the capping member.

The components of an inventive graft construct (e.g., an elongate plug member and a capping member), whether formed separately or together as a single unit, can be constructed in any suitable manner, for example, using any of the processes described herein. In some embodiments, an elongate plug member and a capping member are formed with a reconstituted or otherwise processed ECM material. Elongate plug members and capping members can also be formed by folding or rolling, or otherwise overlaying one or more portions of a biocompatible material, such as a biocompatible sheet material. The overlaid biocompatible sheet material can be compressed and dried or otherwise bonded into a volumetric shape such that a substantially unitary construct is formed. In some forms, an inventive graft component such as the elongate graft body is constructed by randomly or regularly packing one or more pieces of single or multilayer ECM sheet material within a mold and thereafter processing the packed material. Elongate plug members useful in the invention can be prepared, for example, as described in International Patent Application Serial No. PCT/US2006/16748, filed Apr. 29, 2006, and entitled "VOLUMETRIC GRAFTS FOR TREATMENT OF FISTULAE AND RELATED METHODS AND SYSTEMS" (Cook Biotech Incorporated), which is hereby incorporated by reference in its entirety.

When formed separately, a capping member may or may not be comprised of the same biocompatible material(s) as the elongate plug member (or, if present, another capping member). In certain aspects, the elongate plug member and/or any capping member present are comprised of a remodelable material, and in some cases a remodelable collagenous material. Illustratively, a capping member and an elongate plug member can be formed from separate pieces of remodelable, collagenous material (e.g., remodelable SIS material), and thereafter coupled to one another in accordance with the present invention. In certain embodiments, the elongate plug member can be formed of lyophilized ECM material, and the capping member can be formed of a stiffer ECM material, such as an air-dried or vacuum pressed ECM material. In advantageous embodiments, the capping member can be formed of a vacuum pressed, multi-laminate ECM construct, for example having from about two to about ten ECM layers bonded to one another.

As well, inventive graft products and their components can exhibit any suitable size and shape for treating gastrointestinal fistulae and other bodily openings and passageways. An elongate plug member may either have a constant or varying cross-sectional area along its length. For example, elongate plug members useful in the invention may exhibit a generally cylindrical shape, a conical shape, a shape having tapered and non-tapered longitudinal portions, or other suitable shapes having rectilinear and/or curvilinear portions. Also, as discussed in more detail below, some elongate graft bodies of the invention can have one or more lumens extending at least partially through the bodies along their length. A capping member can include one or more objects (e.g., pieces of material) that, together or alone, exhibit a three-dimensional rectilinear or curvilinear shape. Suitable three-dimensional rectilinear shapes can have any suitable number of sides, and can include, for example, cubes, cuboids, tetrahedrons, prisms, pyramids, wedges, and variations thereof. Suitable three-dimensional curvilinear bodies can include, for example, spheres, spheroids, ellipsoids, cylinders, cones, and any suitable variations thereof (e.g., a segment of a sphere, or a truncated cone, etc.). Capping members useful in the invention can be prepared, for example, as described in International Patent Application Serial No. PCT/US2007/061371, filed Jan. 31, 2007, and entitled "FISTULA GRAFTS AND RELATED METHODS AND SYSTEMS FOR TREATING FISTULAE" (Cook Biotech Incorporated), which is hereby incorporated by reference in its entirety.

Illustrative elongate plug members of the invention will be of sufficient size and shape to extend into at least a portion of a fistula tract, and will generally (but not necessarily) be of sufficient dimension to fill a fistula, or a segment thereof, e.g., the primary fistula opening, a fistula tract, and/or any secondary fistula openings, either alone or in combination with other similar or differing devices. In certain embodiments, the elongate plug member will have a length of at least about 0.20 cm, and in many situations at least about 1 cm to about 20 cm (approximately 1 to 8 inches). In illustrative embodiments, the plug member will have a length of from about 2 cm to about 5 cm, or alternatively, from about 2 inches to about 4 inches. Additionally, in certain embodiments, elongate plug members will have a diameter, which may or may not be constant along their length, of from about 0.1 mm to about 25 mm, or more typically from about 5 mm to about 10 mm. In certain embodiments, a generally conical plug member is tapered along its length so that the end of the plug member proximate the capping member has a diameter of about 5 mm to about 10 mm and the opposite end of the plug member has a diameter of about 0.5 mm to about 3 mm. Such a taper may or may not be continuous along the length of the elongate plug member.

The elongate plug member may comprise a compliant sheet form biocompatible material comprising two or more layers of ECM material bonded together. This sheet form elongate plug member can be coupled to or otherwise joined with any of the capping members described herein, for example, the capping member of FIG. 1. This sheet form plug member can be prepared, for example, as described in International Patent Application Serial No. PCT/US2006/16233, filed Apr. 29, 2006, and entitled "FISTULA GRAFT WITH DEFORMABLE SHEET-FORM MATERIAL" (Cook Biotech Incorporated), which is hereby incorporated by reference in its entirety.

The sheet form material is deformable upon impingement by soft tissue surrounding a fistula (e.g., tissue surrounding the primary fistula opening, the fistula tract, and/or any secondary fistula openings) and/or upon impingement by walls of the lumen of a delivery device. Such deformable materials can include any of the ECM or other biocompatible materials described herein, for example, a multilaminate sheet of remodelable SIS material. Further, the sheet form plug is sized and shaped so as to be deformable to a three-dimensional volumetric body extending into at least a portion of the fistula tract, and potentially filling at least a portion of the fistula tract, the primary opening, and/or any secondary openings of the fistula. In so doing, advantageous implant materials will also be sufficiently flaccid to avoid substantial cutting or tearing of the surrounding soft tissues.

In certain aspects, a sheet form graft body is shaped and sized such that the diameter of the primary opening is less than the width of the sheet so that the sheet of material as deployed in the fistula tract is folded and/or rolled over itself one or more times to conform to soft tissues surrounding the fistula and lodge within the fistula tract. Such lodging in place may be sufficient to obviate the need for otherwise securing the graft to the soft tissues at or near the primary opening, fistula tract, and/or any secondary openings. Nonetheless, in certain aspects, the graft is further secured to such soft tissues, for example, by suturing.

Inventive graft body formation methods can involve manipulating graft material within a mold or form. It should be noted that the graft material may or may not be hydrated when placed in, on, around, etc. a mold or form. In some methods, a substantially dry ECM material (e.g., a powder or sheet material) can be placed in a mold and then suitably hydrated for further processing. In other methods, a hydrated starting material is placed in and/or on a mold or forming structure for further processing. For example, one or more hydrated sheets of ECM material can be applied to a form, e.g., wrapped at least partially around a mandrel so that portions of the sheet(s) overlap. Then, the one or more sheets can be dried, and in some embodiments, dried while under compression, to form a unitary graft construct. In some modes of operation, a hydrated graft material is provided within a single- or multiple-part mold having a plurality of apertures or holes extending through a wall of the mold, thereby providing access to the mold interior from an external location. These apertures can serve to enhance drying of a hydrated material during a processing step and in processes exerting vacuum pressure at these apertures, can promote and/or facilitate formation of surface protuberances on the graft material as portions of the same are drawn toward the apertures while under vacuum. In one aspect, an amount of ECM material is retained in such a mold, and needles or other material-displacing objects are inserted through some or all of the mold apertures and a distance into the ECM material, thereby displacing volumes of the ECM material. This can be performed when the graft material is hydrated, partially hydrated or dehydrated. In some forms, with needles inserted in a hydrated ECM material and providing passages therein, the material is subjected to conditions (e.g., freezing and/or dehydrating conditions) which, alone or in combination with one or more other conditions, cause or allow the passages to be generally retained in the ECM material after the needles are removed.

In one embodiment, one or more sheets of hydrated ECM material are suitably wrapped and/or randomly packed around a mandrel, and then a mold having a plurality of holes extending through a wall of the mold is placed around the material-covered mandrel, for example, so that an amount of pressure is placed on the ECM material. The mandrel can then optionally be removed. Thereafter, needles or other material-displacing objects are inserted through some or all of the holes and at least partially through the ECM material, thereby displacing volumes of the ECM material. The ECM material is then at least partially dried. In some aspects, a suitable lyophilization technique is employed, e.g., one with or without a pre-freezing step as described herein. In these or other drying methods in which needles or other penetrating elements are to be left within the mass during drying, these elements can optionally be provided with a plurality of apertures or holes or can otherwise be sufficiently porous to facilitate the drying operation by allowing the passage of hydrate from the wet mass. In one embodiment, a hydrated ECM material with emplaced needles can be subjected to freezing conditions so that the material and any contained hydrate become substantially frozen. Thereafter, the needles can be removed from the ECM material, and the remaining construct (with the frozen material passages substantially retaining their shape) can be placed under a vacuum so that the frozen hydrant sublimes from the material, thereby resulting in a dry graft construct with retained passages therein.

In other modes of operation, passage-forming structures can be incorporated integrally into a mold so that passageways are formed upon introducing the starting material in and/or on the mold. In these aspects, the passage-forming structures can be part of the mold (e.g., extend from a surface of the mold), or they can be separate objects attached or otherwise coupled to the mold, to provide the desired passage or passages through the ultimately-formed graft body.

Although not necessary to broader aspects of the invention, in some aspects, the formation of such a graft construct comprises wrapping one or more sheets of hydrated graft material around a mandrel a number of times. The resulting roll of graft material is then introduced into a mold, and the mandrel is removed (optional), e.g., before or after applying the mold. Thereafter, multiple material-displacing objects such as but not limited to needles are forced through apertures in the mold and into the hydrated graft material, and the material is subjected to one or more drying techniques such as a lyophilization process. In other aspects, the formation of such a graft construct includes placing a flowable graft material into a mold and then subjecting the graft material to further processing. For example, a flowable ECM material mass, such as a gel, paste or putty, potentially incorporating a particulate ECM material, can be placed into a mold, and then with volumes of material displaced in the mass (e.g., by penetrating needles), the ECM material can be dried or otherwise caused to form an integral piece to provide a graft body having passages therein. Illustratively, each of the passages can be provided by forcing a single object through the material mass, or alternatively, where a mandrel is left in place to form a longitudinal lumen, by forcing two objects into the mass and toward one another from opposite directions until they abut the mandrel. The mass can then be processed to a solid graft body as discussed herein.

When implanted in accordance with the present invention, and thus contacting portions of the alimentary canal wall adjacent to the primary opening, the capping member may or may not have a portion extending into the primary opening. For example, in some aspects, the graft body is configured so that no portion of the capping member resides within the primary opening when the graft body is implanted, while in other aspects, the graft body is configured so that a portion of the capping member does reside within the primary opening when the graft body is implanted. Also, it should again be noted that the graft body as a whole, i.e., the combination of the capping member and the elongate plug member, is configured to block at least the primary opening of a fistula. However, neither the capping member portion of the graft body nor the elongate plug member portion of the graft body need be configured to block the primary fistula opening independent of the other member, although either member may be so configured. Additionally, the capping member portion of the graft body, by itself, may or may not be configured to block the fistula tract. In this regard, blocking a particular space or void can be accomplished by filling that space with the capping member, or a portion thereof. In certain aspects, the capping member can be configured to fill the primary opening and/or a portion of the fistula tract. Such filling can, in some embodiments, seal off or substantially seal off the primary opening and/or a portion of the fistula tract.

When suitably implanted, and thus extending into at least a portion of the fistula tract, the elongate plug member may or may not have a portion extending into the primary opening. For example, in some aspects, the graft body is configured so that at least a portion of the elongate plug member resides within the fistula tract but no portion of the elongate plug member resides within the primary opening when the graft is implanted. In other aspects, the elongate plug member is configured to extend through the primary opening and into at least a portion of the fistula tract when the graft body is implanted. Again, in certain embodiments it is the graft body as a whole, i.e., the combination of the capping member and the elongate plug member, that is configured to block at least the primary opening of a fistula. Neither the capping member portion of the graft body nor the elongate plug member portion of the graft body need be configured to block the primary opening independent of the other member, although either member may be so configured. Additionally, the elongate plug member portion of the graft body, by itself, may or may not be configured to block the fistula tract. Further, the elongate plug member portion, by itself, may or may not be configured to block any secondary fistula opening. In this regard, blocking a particular space or void can be accomplished by filling that space with the elongate plug member, or a portion thereof. In certain aspects, the elongate plug member can be configured to fill the primary opening, the fistula tract (or any portion thereof), and/or any secondary openings of the fistula. Such filling can, in some embodiments, seal off or substantially seal off the primary opening, the fistula tract (or any portion thereof), and/or any secondary opening of the fistula.

In certain aspects, the medical graft product comprises a material receptive to tissue ingrowth. In such aspects, upon deployment of the product in accordance with the present invention, cells from the patient can infiltrate the material, leading to, for example, new tissue growth on, around, and/or within the medical graft product. In some embodiments, the medical graft product comprises a remodelable material. In these embodiments, the remodelable material promotes and/or facilitates the formation of new tissue, and is capable of being broken down and replaced by new tissue in such a way that the original fistula closure achieved by the implanted graft product is maintained throughout the remodeling process so as to eventually form a closure or substantial closure with the new tissue.

Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue.

In this regard, any component of a medical graft product of the invention (including any ECM material) can have a level or degree of porosity. In certain embodiments, the porosity of a layer of ECM material is lowered by drying the material under compression. In general, compressing a pliable open matrix material, such as a pliable ECM material, increases the material's bulk density and decreases the material's porosity by decreasing the size of the voids in the open matrix. As is the case in certain aspects of the invention, when such a material is dried while being compressed, particularly under vacuum pressing conditions, the open matrix structure can become somewhat fixed in this relatively higher bulk density, lower porosity state (i.e., in a relatively more collapsed state). It should be noted that different compressing and drying techniques and/or methods, including different degrees of compressing and drying, can be designed through routine experimentation so as to allow for a material layer having an optimal degree of material bulk density and/or porosity for a particular application or procedure.

In certain aspects, a medical graft product of the invention includes at least two regions exhibiting differing properties, e.g., differing porosities. Such differing regions can be established in certain locations, for example, locations providing a particular arrangement or pattern on and/or within the medical product, and in some forms, such differing regions are formed by subjecting the medical product to a suitable differential drying process. Illustratively, a graft body can be configured so that the capping member occupies a more diminished porosity region, while the elongate plug member occupies a more open porosity region. In this configuration, the diminished matrix region can help isolate the fistula tract from the alimentary canal, thus inhibiting bacteria and other undesirable substances from passing into the alimentary canal from the fistula, while the more open matrix region serves to promote more rapid closure of the fistula with its desirable remodeling properties.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

Figure 1B:
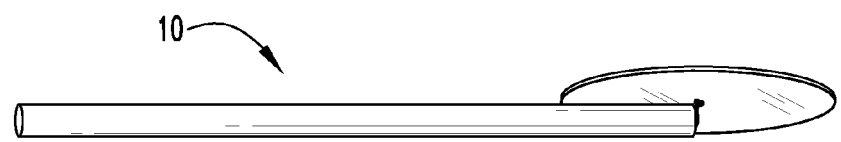
FIG. 1B is a perspective view of the medical graft product illustrated in FIG. 1A where the capping member is folded over the elongate plug member to provide an intermediate configuration.
Figure 1C:
FIG. 1C is a perspective view of the medical graft product illustrated in FIG. 1B where the capping member is rolled around the elongate plug member to provide an implantable configuration.
Figure 1D:
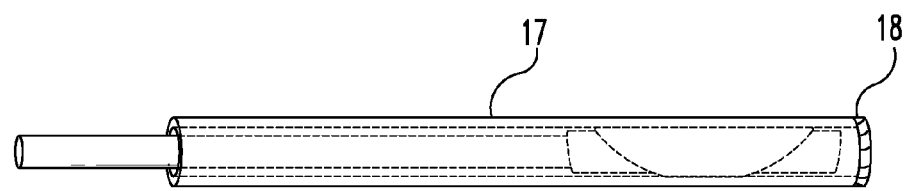
FIG. 1D is a perspective view of the medical graft product in its implantable configuration as illustrated in FIG. 1C where the capping member is folded and rolled over the elongate plug member and is inserted into a sheath for delivery.

With reference now to FIGS. 1A-1D, shown are perspective views of an illustrative medical graft product 10 of the present invention. More specifically, FIG. 1A represents the medical graft product 10 its original configuration, FIG. 1B represents the medical graft product 10 in an intermediate configuration, FIG. 1C represents the medical graft product 10 in its implantable configuration, and FIG. 1D illustrates the medical graft product 10 in its implantable configuration being inserted into a deployment device 17. The medical graft product 10 includes a biocompatible graft body 11 that is configured to block at least the primary opening of a fistula. The graft body 11 includes a capping member 12 and an elongate plug member 13, which extends from the capping member 12. The elongate plug member 13 includes a proximal end 15 and a distal end 16. The capping member 12, which is formed with an ECM material (e.g., SIS), is generally in the shape of a disk and is configured to contact portions of the alimentary canal wall adjacent to the primary opening, particularly those openings occurring within the stomach and/or intestines. The elongate plug member 13, which is also formed with an ECM material, is generally in the shape of a cylinder and is configured to extend into at least a portion of the fistula tract. The capping member 12 is hingedly coupled to the distal end 16 of the elongate plug member 13 by suture 14. It should be noted that the elongate plug member 13 (and any other plug member described herein) may or may not be sized and shaped to fill an entire fistula tract.

With regard to the intermediate configuration, FIG. 1B illustrates the medical graft product depicted in FIG. 1A where the capping member 12 is swung over the elongate plug member 13 from distal end 16 towards proximal end 15. This process is made possible by the hinged coupling of the capping member 12 to the distal end 16 of the elongate plug member 13. Typically, the capping member 12 will be loosely coupled to the elongate plug member such that the capping member 12 can be easily folded over the elongate plug member by a practitioner or during a manufacturing process. Once positioned at least partially overlapping plug member 13, the capping member 12 can be rolled or wrapped around the elongate plug member 13 as shown in FIG. 1C to arrive at the implantable configuration. In the implantable configuration shown, device 10 includes a portion of the capping member 12 conformed around plug member 13 and a leading portion of capping member 12 extending distally beyond the distal end of plug member 13. Other configurations in which at least a portion of the capping member 12 is conformed to the outer surface of plug member 13 can also be used. Once in its implantable configuration, the medical graft product 10 can be inserted into deployment device 17 and can be implanted within a patient so that capping member 12 contacts portions of alimentary canal wall adjacent to a primary opening, and the elongate plug member 13 extends into at least a portion of fistula tract. To facilitate visualization during deployment, deployment device 17 can have a radiopaque band 18 or other marker positioned at its distal end. In this manner, fluoroscopic imaging can be used to track the position of the distal end of delivery device 17, for instance to identify the point at which such distal end has entered the alimentary canal. Once the medical graft product is delivered, the capping member can regain its original shape or otherwise expand and thus contact portions of an alimentary canal wall adjacent to the primary opening of a fistula when graft 11 is pulled proximally.

Figure 1E:
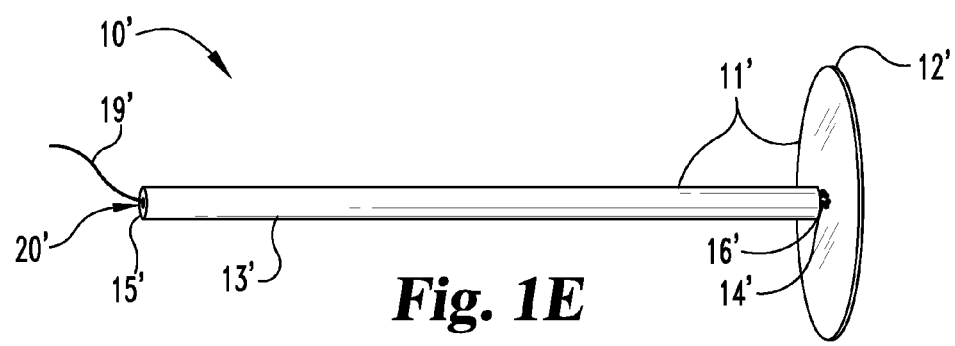
FIG. 1E is a perspective view of an illustrative medical graft product including an elongate body, a capping member, and a pull tether.

An alternative graft embodiment 10' is depicted in FIG. 1E. This graft device is similar to that depicted in FIGS. 1A-1D, except that it also includes a suture material or another tether 19' passed through a central lumen 20' and attached to the capping member. This tether can provide means for adjusting the position of the device during and/or after deployment, and potentially also provide means for anchoring the device, for example, by suturing device 10' to patient tissue at or adjacent to a fistula opening. In one mode of use, after deployment of graft 10' from the lumen of a delivery device as discussed above, tether 19' can be used to pull graft device 10' in a proximal direction to lodge capping member 12' against the wall of the alimentary canal. For these purposes, it will be understood that other modes of attachment of tether 19' to any suitable location of graft device 10' could be used, so long as they enable repositioning the graft device 10' by pulling on the tether 19'.

In another form, a graft device having a lumen such as that depicted in FIG. 1E, the lumen also extending through capping member 12', can be delivered over the wire in order to treat the fistula. Such a graft device can have tether 19' or can optionally lack the tether 19'. Delivery over the wire can be facilitated using a cannulated pusher to force the graft device 10' along the wire, e.g. starting from the fistula opening in the skin and continuing until the capping member 12' enters the alimentary canal and expands, generally as discussed above. In such embodiments, the presence of a tether attached at some point to the device 10' (e.g. to the capping member as depicted at or near the proximal end of device 10' opposite the capping member) can provide a means by which the device 10' can then be pulled proximally to lodge capping member 12' against the canal wall.

In certain forms of the invention, a graft product incorporates an anchoring adaptation to maintain the capping member in contact with portions of the alimentary canal wall adjacent the primary opening following product implantation. For example, the medical graft product of the invention can include an adhesive for maintaining this type of contact. Adhesive can be applied to the graft product before an implantation procedure, e.g., during manufacture of the product, or alternatively, can be applied to the graft product and/or to tissue at or near the primary opening during such an implantation procedure. Other suitable anchoring adaptations include but are not limited to barbs, hooks, sutures, protuberances, ribs, and the like. Again, such anchoring adaptations, while advantageous in certain forms of the invention, are not necessary to broader aspects of the invention. Illustratively, certain medical graft products are configured so that the capping member is able to maintain contact with portions of the alimentary canal wall adjacent to the primary opening following implantation without the need for such anchoring adaptations. In other aspects, suitable anchoring adaptations aid or facilitate the maintenance of such contact. In embodiments where the capping member is constructed so as to fit within a deployment device, such as the one depicted in FIGS. 1A-1D, such anchoring adaptations will be selected so as not to interfere with this process (i.e., the anchoring adaptations, if any, will not obstruct the medical graft product from being easily loaded and deployed from said deployment device).

In certain aspects, the invention provides biocompatible graft bodies that include an expandable element (e.g., an expandable material and/or device). In this regard, inventive graft bodies may be provided, wherein the capping member, the elongate plug member, or both have the capacity to expand. For example, the capping member and/or the elongate plug member can include, for example, a suitable ECM foam or sponge form material. Illustratively, a graft body, or any portion thereof, may comprise a porous, three-dimensionally stable body formed with one or more suitable biocompatible matrix materials. Such biocompatible matrix materials can include naturally-occurring polymers and/or synthetic polymers. More preferred sponge compositions will comprise collagen as a matrix-forming material, either alone or in combination with one or more other matrix forming materials, and particularly preferred sponge compositions will comprise an ECM material such as those discussed elsewhere herein. In general, sponge matrices useful in certain embodiments of the present invention can be formed by providing a liquid solution or suspension of a matrix-forming material, and causing the material to form a porous three-dimensionally stable structure; however, a sponge or foam material can be formed using any suitable formation method, as is known in the art. For additional information concerning foam or sponge form materials that can be useful in certain embodiments of the present invention, reference can be made, for example, to U.S. Pat. App. Pub. No. 2003/0013989.

In some forms, a compact, stabilized sponge construct used to form the elongate graft body and/or capping member is highly expansive when wetted, which can desirably enhance the ability of the graft body to block (and to continue blocking) at least the primary opening of a fistula.

In illustrative procedures, a suitable hydrant, such as saline, may be applied or delivered to the graft body after it is suitably located within a patient to enhance the expansion of the body within the fistula tract and/or a fistula opening. Alternatively, or additionally, a bodily fluid of the patient can sufficiently wet the implanted graft body so as to promote the expansion of the body within the fistula.

These compact, stabilized sponge constructs and other expandable graft body elements, when used in the invention, can allow the graft body to attain a more low-profile configuration during a deployment step. For example, an illustrative deployment system can include a graft body, wherein the capping member (and optionally also the elongate plug member) is comprised of an expandable device and/or material such that in a stabilized, compressed first configuration, the graft body can fit within an end of a delivery device (e.g., a probing device, delivery sheath, or other similar instrument), which is sized and configured to traverse a fistula tract. Illustratively, this end of the delivery device can be passed into a secondary opening, through a fistula tract, and out of a primary opening into the alimentary canal. Thereafter, the graft body (or at least the capping member portion of the graft body) can be pushed or otherwise removed from the delivery device in a suitable manner to allow the capping member to attain an expanded second configuration. In such an expanded configuration, the capping member, which was previously able to traverse the primary fistula opening, is now sized and shaped to contact portions of the alimentary canal wall adjacent the primary opening so that at least a portion of the capping member cannot pass back through the primary opening.

Additionally, in illustrative embodiments, one or more anchors, barbs, ribs, protuberances, and/or other suitable surface modifications can be incorporated on and/or within an illustrative graft body to roughen, condition, or otherwise deepithelialize at least a portion of the fistula, such as the fistula tract and/or the primary opening, during and/or after emplacement of the graft within the tract. The conditioning of the tract tissue can serve to initiate a localized healing response in patient tissue that can be advantageous in enhancing the ingrowth of patient tissue into an illustrative plug construct, such as a plug comprising an ECM material. Further, in illustrative embodiments, where a suture, leader, or string is used to assist with the emplacement of an illustrative graft construct within a tract, as is discussed elsewhere herein, the leader can comprise an abrasive material, or comprise one or more sections and/or surface features and/or adaptations, e.g. one or more bristles that can directionally emanate from the leader material and that can serve to roughen or otherwise condition or de-epithelialize patient tissue upon travel through and/or location within a fistula tract.

In certain aspects, medical graft products of the invention incorporate an adhesive or, where appropriate, a sclerosing agent to facilitate and/or promote blocking of at least the primary opening of the fistula. As well, fistula treatment methods of the invention can include steps where such substances or materials are applied to a medical graft product being deployed and/or to the soft tissues surrounding the fistula. For example, an adhesive, glue or other bonding agent may also be used in achieving a bond between a medical graft product of the invention and the soft tissues defining a fistula opening or tract and/or adjacent tissues. Suitable bonding agents may include, for example, fibrin or collagen gels or pastes, gelatin, or other agents including reactive monomers or polymers, e.g., cyanoacrylate adhesives. In some forms of the invention, a fistula treatment method includes contacting soft tissue surfaces surrounding the fistula, e.g., soft tissue surfaces at or near the primary opening and/or soft tissues lining the fistula tract, with a sclerosing agent prior to forcing the sheet from material into the fistula. Such use of a sclerosing agent can deepithelialize or otherwise damage or disrupt these soft tissue surfaces, leading to the initiation of a healing response.

A plurality of passages formed or otherwise occurring in a graft body may be present in any suitable number in an inventive product. These passages can exhibit a variety of shapes and sizes, and can extend through all or a portion of the body. In some forms, one or more passages extend from a graft body surface and includes a generally coherent passage wall. Illustratively, a tubular graft body having an internal lumen extending through the body along its length can have passages extending partially or entirely through a wall of the tube, e.g., from an exterior surface to an interior surface of the tube wall. Also, the spacing and size of a passage in a graft body relative to another passage in the body, as well as the depth to which a particular passage extends into a graft body, can vary. In some forms, the passages are generally cylindrical voids, e.g., having diameters ranging from about 0.05 mm to about 15 mm, more typically from about 0.10 mm to about 5 mm, and even more typically from about 0.1 mm to about 1.0 mm. These and other graft body passages useful in the present invention can be spaced any suitable distance from one another, and in some embodiments, are positioned in a particular pattern (e.g., in rows), although a plurality of passages can be randomly placed as well. Further, a plurality of passages in a construct can be configured so that any one passage extends the same or a different distance into the construct relative to any other passage in the construct.

Further in this regard, passages occurring in a graft body may be formed in any suitable manner. In some embodiments, passages can be created in a graft body after the graft body is formed, e.g., after a cast collagenous material is dried to form a coherent body. In some embodiments, at least part of the formation of some or all of the passages in a graft body occurs during formation of the graft body. Illustratively, an inventive method can include a step where a passage is initially provided in a hydrated material mass, e.g., by displacing a volume of material in the mass. Then, with the passages present in the hydrated material mass, the mass can be subjected to suitable drying conditions (e.g., a lyophilization step) to cause or allow the passages to be retained in the dried graft body. It should be noted that a hydrated material in such processes (e.g., a reconstituted or naturally-derived collagenous material) can have a level of hydration including full or partial hydration, and in this regard, a drying process can be used to lower starting material hydration to any suitable level including substantially dehydrated. Also, displacing a volume of material in a hydrated mass of material to create a passage can be accomplished in a variety of manners, and in certain aspects, involves forcing or otherwise introducing an implement or other material-displacing object (e.g., a cannulated or non-cannulated needle) into the mass. Other suitable material-displacing objects can be selected according to the type of passage desired.

Turning now to a general discussion regarding methods of the invention for treating fistulae, suitable treatment methods include providing a medical graft product such as any of those described above, and implanting the product within a patient so that: (i) the graft body blocks at least the primary opening of a fistula, i.e., the primary opening and potentially one or more other segments of a fistula, for example, the fistula tract and/or any secondary openings; (ii) the capping member contacts portions of the alimentary canal wall adjacent to the primary opening; and (iii) the elongate plug member extends into at least a portion of the fistula tract. In some modes of operation, the distal end of a deployment device can be inserted into a fistula, for example, into a secondary opening, through a fistula tract, and a distance out of the primary opening. Thereafter, the graft body (or at least the capping member) can be removed from the device, for example with a push rod or other suitable device, allowing the capping member to expand or to at least retain its original shape prior to loading of the graft body into the deployment device. Then, the graft body can be pulled back through the fistula tract until the capping member contacts portions of the alimentary canal wall adjacent to the primary opening. The delivery device can then be withdrawn from the fistula through the secondary opening, leaving the deformed sheet-form material deployed within at least a portion of the fistula tract, and potentially filling at least a portion of the fistula tract, the primary opening, and/or any secondary openings of the fistula.

Products and methods of the invention can be used to treat any fistula, and in particular embodiments, fistulae having a primary opening in a wall of the alimentary canal, such as those occurring in the stomach or intestine. In some aspects, the invention provides medical graft products and methods useful for blocking openings anywhere on or within the body of a patient, for example, blocking at least the primary opening of a urethro-vaginal fistulae, vesico-vaginal fistulae, tracheoesophageal fistulae, gastrointestinal fistulae, and any number of anorectal fistulae, such as recto-vaginal fistula, recto-vesical fistulae, recto-urethral fistulae, or recto-prostatic fistulae. In preferred embodiments, the medical graft products of the invention are designed to treat a gastrointestinal fistula, such as an enterocutaneous fistula. Also, inventive products and methods can be used to treat a fistula regardless of its size and shape, and in some forms, are utilized to treat a fistula having a primary opening, secondary opening, and/or fistula tract with a diameter ranging from about 1 millimeter to about 20 millimeters, more typically from about 5 millimeters to about 10 millimeters.

Medical products of the invention can be implanted using any suitable delivery method or placement technique. Illustratively, a graft body can be implanted by pulling or pushing the graft body into a suitable position within a fistula. For example, the elongate plug member end of the body can be pulled toward a secondary opening within the fistula tract (e.g., through the primary opening and into the fistula tract) until the capping member contacts portions of the alimentary canal wall adjacent to the primary opening. In certain embodiments, such pulling can be accomplished using a fistula probe or other suitable instrument, for example, an appropriately configured pair of surgical hemostats that include a portion passable into a secondary opening, through the fistula tract, and potentially out of the primary opening. Thereafter, the elongate plug member portion of the graft body can be releasably grasped by the probe or otherwise coupled to the probe and pulled into the primary opening. In other embodiments, an illustrative graft body is suitably deployed using a biocompatible sheath or catheter, which can be configured to traverse the tract of a fistula, and is optionally located within the fistula tract over a suitable wire guide or under endoscopic guidance. In these embodiments, an illustrative graft construct can be deployed in an over-the-wire configuration or through an unobstructed sheath lumen. In addition to those described elsewhere herein, suitable delivery devices and systems useful in such embodiments of the invention can be prepared and used, for example, as described in International Patent Application Serial No. PCT/US2007/061380, filed Jan. 31, 2007, and entitled "FISTULA GRAFT DEPLOYMENT SYSTEMS AND METHODS" (Cook Biotech Incorporated), which is hereby incorporated by reference in its entirety.

Fistula treatment methods of the invention may include an endoscopic visualization (fistuloscopy) step. Such endoscopic visualization can be used, for example, to determine the shape and size of the fistula, which in turn can be used to select an appropriately sized and shaped medical graft product for treating the fistula. Illustratively, a very thin flexible endoscope can be inserted into a secondary opening of the fistula and advanced under direct vision through the fistula tract and out through the primary opening. By performing fistuloscopy of the fistula, the primary opening can be accurately identified. Also, cleaning of the fistula can be performed prior to and/or during deployment of a medical graft product of the invention. For example, an irrigating fluid can be used to remove any inflammatory or necrotic tissue located within the fistula prior to engrafting the product. In certain embodiments, one or more antibiotics are applied to the medical graft product and/or the soft tissues surrounding the fistula as an extra precaution or means of treating any residual infection within the fistula.

The present invention also provides, in certain aspects, medical products that include a radiopaque element such as but not limited to a radiopaque coating, attached radiopaque object, or integrated radiopaque substance. In this regard, the capping member and/or elongate plug member of some inventive graft bodies may be comprised of a radiopaque element so that, for example, the movement of the product may be monitored and the product may be placed at a desired location. Any suitable radiopaque substance, including but not limited to, tantalum such as tantalum powder, can be incorporated into a medical product of the invention. Other radiopaque materials comprise bismuth, iodine, and barium, as well as other suitable markers.

The capping members described herein can be shaped and configured in a variety of manners. In some instances, a capping member includes a resilient wire frame or other similar frame or frame-like support device. These devices can, in some embodiments, be designed to move between a first device configuration and a second device configuration, for example, in the case of a frame that is compactable to a compacted, first condition, and when in this compacted condition, is then expandable to an expanded, second condition. In forms where a frame has the capacity to expand, these frames can include those that are self-expanding and those that require at least some manipulation in order to expand. In certain embodiments, an inventive support frame is unable to freely fit inside a delivery device lumen when in a first condition (e.g., in a generally relaxed state), but then can be manipulated into a second condition for placement in the lumen. In the lumen, the frame is constrained by interior device surfaces that define the lumen. Upon removal from the lumen, the frame then generally returns to the first condition.

Figure 2A:
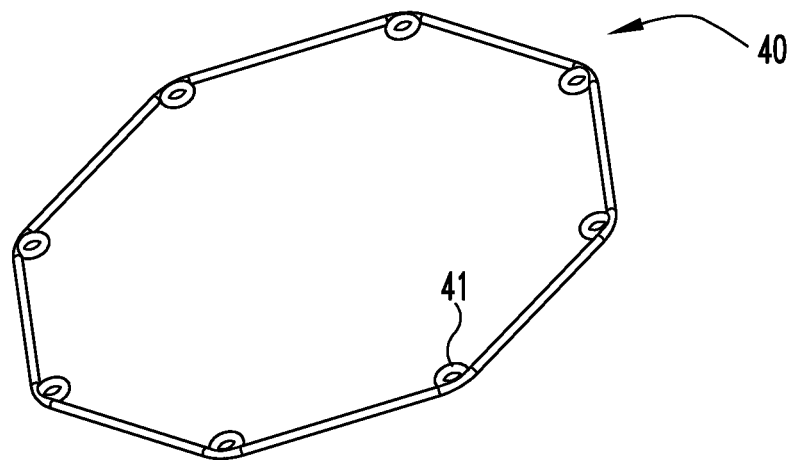
FIG. 2A is a perspective view of a support frame useful in the present invention.

With reference now to FIG. 2A, shown is a support frame 40 which can be incorporated into a grafting device of the invention. Support frames of this sort and other similar devices useful in the present invention can be constructed using one or more pieces of stainless steel wire, super elastic wire or any of a variety of other suitable materials described herein or otherwise known to those skilled in the art. In this particular embodiment, support frame 40 includes a single piece of Nitinol wire having a plurality of sides and bends interconnecting adjacent sides. Bends of this sort can include coils, fillets, or other suitable configurations, for example, those designed to reduce stress and fatigue. Support frame 40 incorporates optional bend adaptations 41 having apertures occurring therein as generally shown. The single piece of wire is preferably connected to itself by an attachment mechanism, such as a piece of cannula and solder, to form a closed circumference frame. In some aspects, a closed circumference frame (e.g., an octagonal frame) rather than being constructed by joining together parts of one or more other objects (e.g., ends of a single piece of wire) is instead formed as a closed circumference frame, for example, as a unitary device in a mold or form, or developed from a larger piece of material (e.g., laser cut from a metallic sheet of material). While a preferred frame embodiment is an eight-sided polygon such as that shown in FIG. 2A, other shapes having rectilinear and/or curvilinear components are contemplated as well, for example, circular or oval shapes or other polygonal shapes having three, four, five, six, seven or any suitable number of sides.

Support frame 40, which is shown in a relaxed condition in FIG. 2A, is a resilient device. Thus, the frame can be deformed (e.g., collapsed, compressed, etc.) from this relaxed, first condition to a deformed, second condition. In this deformed, second condition, the resilient frame is then poised to essentially return to its relaxed, first condition. Illustratively, support frame 40 can be compressed into a compressed condition (e.g., by folding one or more times and/or rolling portions of the frame) for positioning in a delivery device lumen having a relatively smaller diameter than that which the frame could otherwise fit in its relaxed condition. In this compressed condition, the frame then has the ability to self-expand essentially back to its prior, relaxed condition upon being removed from the delivery device lumen.

In a preferred embodiment, a capping member includes a support frame and a deformable covering material. The support frame and covering material can each be formed with one or more of a variety of materials. Illustratively, a support frame formed with a resilient material (e.g., Nitinol) can be combined with a sheet-form resorbable or nonresorbable material, and in some cases, a multilayered (e.g., remodelable) material, wherein this combination provides a suitable arrangement for blocking, and in some cases sealing off, a fistula opening. Arrangements of this sort include but are not limited to capping members that include a support frame that can lie in a single, generally flat plane, and a sheet-form deformable covering material extending between peripheral regions of the support frame, although a variety of other capping member shapes and configurations are contemplated as within the scope of the present invention. Some of these devices can be used to treat fistulae having a primary opening in a bowel wall, and in this regard, may be effective to block or otherwise exclude the bowel lumen from the fistula tract when desirably deployed. Covering materials can be manipulated before, during and/or after being combined with a support member. In some cases, a covering material will be already-formed before being associated with a support frame. In other cases, a covering material will be fully or partially formed in the presence of a support frame or portion thereof. When present, a covering material that is to be combined with a support device can be attached to or otherwise suitably associated with the support device in a variety of manners including some that involve bonding and/or mechanically fastening the covering material to the device. In some cases, an edge of a covering material is folded over a frame segment and attached to another portion of the material to provide a sleeve or other channel-like adaptation for retaining the covering material in association with the support frame.

Certain embodiments of the invention provide capping members including an expandable or otherwise deformable frame member associated with a full or partial covering of material on one or more surfaces of (e.g., an inner and/or outer surface) of the expandable frame member. In some embodiments, the covering material is associated in a unique manner with the expandable frame member. For example, the covering material may be contoured snugly around or completely or partially embed elements of the expandable frame member to assist in maintaining the attachment of the covering material to the expandable frame member. This may avoid, reduce, or simplify the need for other mechanical attachments, such as sutures, to hold the covering material to the expandable frame member. It may also in some forms provide a unique, relatively fixed association of the covering material with the expandable frame member or elements thereof, even during contraction and/or expansion of the frame. Illustratively, coverings that completely or partially embed a frame member can be made by casting a polymerizable, crosslinkable or otherwise hardenable flowable material onto and around all or a portion of the frame member, and then causing the flowable material to polymerize, crosslink and/or otherwise harden. In some other cases, a flexible material can be positioned around a frame, and then the material physically, chemically and/or otherwise altered (e.g., via lyophilization, heating, etc.) so that the material becomes less flexible for maintaining the material in association with the frame.

Capping member support frames, when used in the present invention, can be associated with one or more of a variety of materials to form effective capping arrangements. Useful covering and other materials for capping purposes include naturally-derived and non-naturally-derived materials such as those described elsewhere herein. Both resorbable and nonresorbable materials may be employed in this regard. In some preferred embodiments, polymeric materials are associated with support structures to form useful capping members. These include synthetic and non-synthetic polymers. These various materials can be applied to or otherwise associated with support members in a variety of manners including some that involve mechanical fastening of an already-formed material, forming material along and/or around portions of the frame (e.g., in a mold or form, by spray coating, dip coating, etc.), thermoforming, solvent dissolution, and variations and combinations thereof.

Figure 2B:
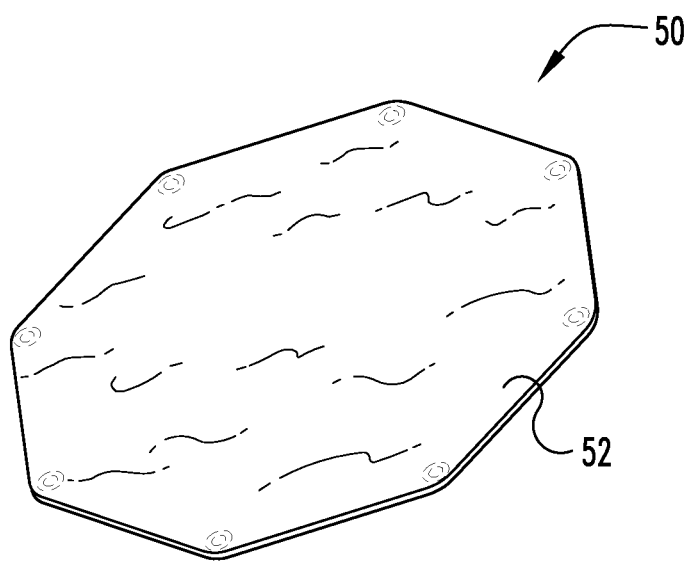
FIG. 2B provides a perspective view of a capping member of the present invention.

In some cases, a flexible covering material that is pulled taught along a collapsible support frame can fold and/or roll along with a frame as it collapses, and upon the frame returning to its prior shape, can also essentially return to its prior condition to again be pulled taught. Referring now to FIG. 2B, shown is a capping member 50 that incorporates the support frame from FIG. 2A. Capping member 50 additionally includes a deformable covering material 52 attached to and extending between opposing, peripheral edges of the frame. In a preferred embodiment, capping member 50 will generally be sized and configured so that when positioned over a fistula opening in a bodily structure wall (e.g., a primary fistula opening in an alimentary canal wall), outer regions of the capping member (i.e., those including the support frame) extend beyond the opening along the bodily structure wall and contact portions of the bodily structure wall adjacent to the opening, and inner regions of the capping member cover and block the opening.

In some cases, a capping member such as capping member 50 will include at least one elongate device (e.g., a suture, plug member, etc.) extending therefrom. For example, an elongate plug can be connected to (e.g., sutured, glued, etc.) covering material 52 such as in a region of the material that is centrally located relative to the support frame perimeter. In this manner, the device can be positioned in a patient such that capping member 50 is positioned over a fistula opening, and the elongate plug member extends into a fistula tract extending from this opening. In this position, the elongate plug member can be pulled away from the capped fistula opening such that portions of deformable covering material 52 are drawn into the fistula tract. Desirably, support frame 40 provides an anchor of sorts for capping member 50 so that as inner regions of covering material 52 are drawn into the fistula tract, support frame 40 and outer regions of covering material 52 remain outside of the fistula tract. In some cases, when a sufficiently flexible covering material is pulled in this manner, portions of the covering material can deform to provide a convex or other similar surface for contacting patient tissue at the fistula opening to seal or substantially seal off the opening.

Figure 3A:
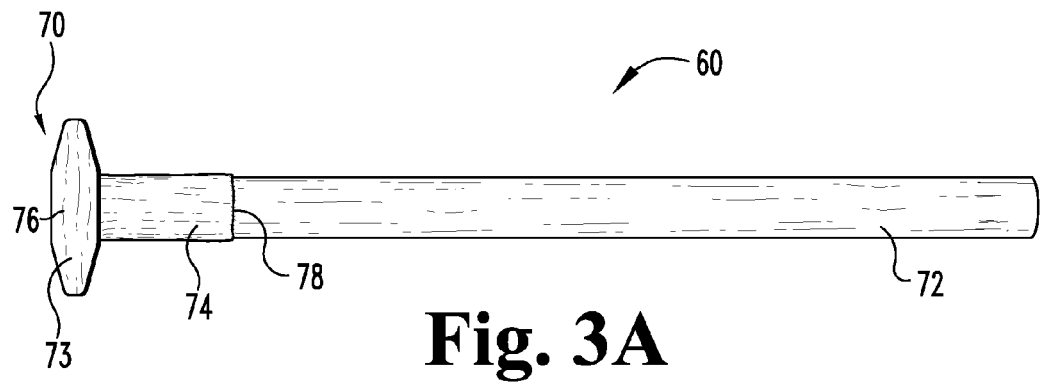
FIG. 3A is a perspective view of a medical graft device of the invention.
Figure 3B:
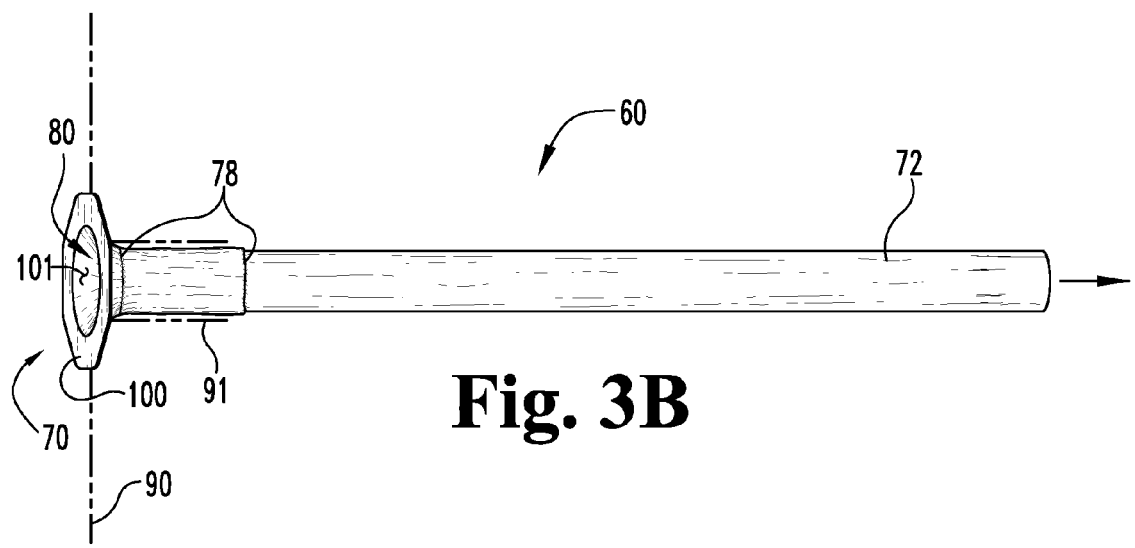
FIG. 3B shows the medical graft device of FIG. 3A implanted within a patient.

FIGS. 3A and 3B show a medical graft device 60 of the present invention that includes a capping member 70 and a generally cylindrical, elongate plug member 72 extending from this capping member. Plug member 72 is configured to extend into and fill at least a portion of a fistula tract, and its dimensions including its length can vary, with those skilled in the art recognizing suitable plug dimensions for a particular application. In some cases, a plug length is provided for extending through an entire fistula tract up to about 15 cm or longer, although such a plug could be cut to size as desired to fit all or a portion of a particular tract. As well, elongate plug member 72 can be formed with one or more of a variety of materials, and in some preferred embodiments, is formed with a rolled sheet-form material such as but not limited to a single- or multi-layered naturally-derived material (e.g., a collagenous ECM material). Capping member 70, which includes a deformable covering material 73, is similar to that shown in FIG. 2B except that it additionally includes a sheath portion 74 extending away (in a generally perpendicular direction) from a centrally-located region of its bottom surface. Capping member 70 includes a top surface 76. Sheath portion 74 is configured to be positioned over and extend along at least a segment of plug member 72 as generally shown in FIG. 3A. A plurality of sutures 78 attach sheath portion 74 to plug member 72, although a variety of other attachments means are contemplated as within the scope of the present invention.

A capping member sheath portion useful in the invention can be formed separately from, and then subsequently united with, the remainder of a capping member, or alternatively, can be formed as part of an existing capping member component. In this particular embodiment, sheath portion 74 comprises a portion of covering material 72 extending away from the remainder of the capping member. Illustratively, a sheath portion of this sort can be formed by providing a covering material sufficiently sized to be wrapped around a support frame with enough material left over on one side to form a sheath or sheath-like capping member component. In some cases, a somewhat flexible material is positioned around a frame in such a manner, and then the material is physically, chemically and/or otherwise treated (e.g., lyophilized, heated, etc.) so that the material becomes less flexible for maintaining the material in the desired configuration.

Referring again to FIG. 3B, in some modes of use, graft device 60 is implanted within a patient such that capping member 70 is positioned over a fistula opening 80 occurring in a bodily structure wall 90, and elongate plug member 72 extends into a fistula tract 91 extending from this opening. In this position, plug member 72 can be pulled in the direction of the arrow shown (i.e., away from the capped fistula opening) such that portions of deformable covering material 73 are drawn into the fistula tract as generally shown. In an alternative embodiment, graft device 60 incorporates a tether extending from elongate plug member 72 (e.g., away from the end opposite capping member 70), which may be useful in manipulating the position the device at certain points during delivery. A tether of this sort may be a suture (e.g., a 2-0 vicryl suture) embedded within, attached to or otherwise associated with plug member 72.

Desirably, the support frame will be sized and configured so that it remains outside of the fistula tract (e.g., along the bodily structure wall in an area extending a suitable distance beyond the fistula opening) even when a considerable amount of pulling force is applied to plug member 72. In this manner, when capping member 70 is deformed as shown in FIG. 3B, the support frame and an externally remaining portion 100 of the covering material will remain outside of the fistula tract, while a portion of the covering material that previously (i.e., prior to deformation) resided outside of the fistula tract will now reside within the fistula tract to provide an internalized covering material portion 101. In some forms, the capping member is deformed so that portions of the covering material very snugly conform to patient tissue at the fistula opening in a generally non-planar condition such as a cupping or cup-like arrangement. The plug member 72 can then be secured in position, e.g., using one or more sutures to patient tissue, to retain the conforming condition of the capping member.

Graft device 60 and other similar inventive devices are particularly suitable for treating enterocutaneous and other gastrointestinal fistulae, although such devices can be adapted to treat a variety of other fistulae as well. These devices can be implanted in any suitable manner. In a preferred embodiment, graft device 60 is placed with the aid of a delivery sheath or other similar delivery device, for example, a splittable sheath as discussed in more detail below. In one mode of operation, the distal end of a wire guide is passed into an enterocutaneous fistula tract through a secondary fistula opening and toward a primary fistula opening under fluoroscopic guidance. The wire is advanced until its distal end enters the alimentary canal through the primary opening. Thereafter, the distal end of an over-the-wire dilator-sheath combination is advanced through the tract in a similar manner, for example, until the sheath is positioned at or just beyond the primary opening. The dilator is then removed, leaving the sheath (e.g., a check-flow sheath) and potentially also the guidewire in the tract. In some cases, the wire guide is removed with the dilator. Then, a suitably sized and shaped graft device such as graft device 60 is loaded into the sheath through its proximal end, for example, with the capping member 70 in a compressed condition (e.g., folded one or more times and/or rolled) entering the sheath first, and elongate plug member 72 following. The plug member may then be fully pushed into the sheath by hand. The capping member, in a compressed condition, is poised to return to its expanded condition upon being removed from the delivery device lumen.

Next, an over-the-wire pusher is introduced into the sheath proximal end and advanced toward the sheath distal end until at least a portion of the graft device is desirably pushed from the sheath distal end (e.g., with capping member 70 in an expanded condition and extending a distance into the alimentary canal). In some cases, the capping member and/or plug member will incorporate a device or material to aid in imaging the device during delivery. Illustratively, a stainless steel button or other similar device may be attached to the end of the plug member near the capping member. As well, a capping member support frame can be formed with a radiopaque material. Alternatively, a support frame can be formed with a resorbable material such as a collagenous ECM material (e.g., SIS), polycaprolactone, polyhydroxyalkanoates- or PHA polymers, etc. with a radiopaque marker attached.

Then, the pusher can be placed in contact with the plug member 72 to provide back pressure, while the delivery sheath is removed, thus maintaining desirable positioning of the device inside the tract. After the sheath and pusher are removed, plug member 72 can be manipulated to achieve a desired deformation of capping member 70, for example, as described above. With capping member 70 desirably deformed, plug member 72 can then be secured in place (e.g., sutured or otherwise fixed to patient tissue at and/or around the secondary fistula opening) to maintain the capping member in this deformed condition. In some cases, the plug member will extend a distance out of the secondary opening when the capping member is deformed. This portion may optionally be trimmed off before or after the plug is secured in place. Although not necessary to broader aspects of the present invention, in the current embodiment, plug member 72 is directly or indirectly attached to the underside of the material defining the capping member top surface 76, and in this regard, internalized covering material portion 101 includes some of the material defining this surface. In one aspect, a support frame is attached to a covering material with resorbable sutures, allowing the frame to separate from the remainder of the graft device after a certain amount of time following initial plug deployment, and pass through and out of the alimentary canal.

In some preferred embodiments, care is taken to not block or otherwise close the secondary opening to facilitate drainage of the tract following the implantation procedure, for example, during remodeling when a remodelable material is utilized in the plugging assembly. Of course, it will be understood that the steps described above can occur in any suitable order as will be recognized by those skilled in the art. For example, a graft device may be preloaded into a delivery device before the delivery device is positioned in a fistula tract. In some cases, when a delivery system component (e.g., a wire guide, dilator, pusher, etc.) is deemed not necessary for a particular delivery application, this component will be excluded from the delivery system and any associated methods of delivery.

FIG. 4A shows a medical graft device 120 according to another embodiment of the present invention. Device 120 includes a capping member 121 and an elongate plug member 122 extending from the capping member. Plug member 122 is configured to extend into and potentially fill a fistula tract. Such a plug member may be formed as described elsewhere herein, for example, as described in regard to the plug member depicted in FIGS. 3A and 3B. In some cases, a plug of this sort will have a length ranging from about 10 cm to about 20 cm, more typically from about 15 cm to about 18 cm.

Capping member 121 is comprised of a deformable material 123 having portions extending between outer edges of an octagonal, resilient support frame 124. Support frame 124 is a closed circumference frame made of Nitinol. In some preferred embodiments, the deformable material is comprised of a polymeric material, e.g., a synthetic polymeric material such as but not limited to polyurethane materials such as THORALON®, thermoplastic silicones, etc. In some instances, a naturally-derived material such as an ECM or other naturally-derived material is additionally or alternatively included. Such materials may be coated with other material(s), for example, a PCL-coated or PLGA-coated collagenous material (e.g., a coated SIS material). Such materials may be fully or partially formed on and/or around a support frame, or alternatively, may be provided as a separate component and then suitably combined with the support frame. In a preferred embodiment, a synthetic polymer is desirably thermoformed around a support frame to fully or partially embed parts of the support frame.

Capping member 121 includes a top surface 127, which is configured to face the bowel lumen when the device is desirably implanted within a fistula. Deformable material 123 also provides a sheath portion 128 extending away (in a generally perpendicular direction) from a centrally-located region of the bottom surface of the capping member. Sheath portion 128 is configured to be positioned over and extend along at least a segment of plug member 122 as generally shown in FIG. 4A. A plurality of sutures 129 attach sheath portion 128 to plug member 122, although a variety of other attachments means are contemplated as within the scope of the present invention. A stainless steel or other suitable radiopaque marker may be incorporated into a distal region of device 120. A tether 130 (e.g., suture material) is attached to the plug body near its proximal end, and can extend proximally away from the plug body to potentially aid in product handling and/or delivery.

Device 120 can be delivered into a fistula tract in any suitable manner including that described above in relation to FIGS. 3A and 3B. In one embodiment, capping member 121 is positioned in a delivery lumen such that a first edge portion of capping member 121 is deflected toward the proximal end of plug member 122, while a second (opposite) edge portion of capping member 121 is deflected generally in the opposite direction (i.e., away from the proximal end of plug member 122). In such a condition, a portion of capping member 121 will overlap or otherwise extend back over and potentially wrap and conform to an exterior, lateral surface of plug member 122, while another portion of capping member 121 will extend out in front of the distal end of plug member 122, although other folding or compaction patterns could be used in certain embodiments. An example of how device 120 can be positioned in a delivery device lumen is depicted in FIG. 4B. So positioned, the capping member is poised to return to its generally non-deformed condition upon being removed from the lumen of delivery device 131.

In some forms, capping member portions, which would otherwise be essentially perpendicular to the longitudinal axis of the plug member when the capping member is in a generally relaxed condition, can be made to reside in a parallel (or closer to parallel) position relative to this longitudinal axis. When positioned in a delivery device lumen, these capping member portions may be constrained by and/or conform to interior walls of the delivery device defining the lumen. As well, any portions of the capping member extending along exterior, lateral surfaces of the plug member may at least somewhat conform to these plug member surfaces.

Plug member 122 is generally cylindrical, with a substantial portion of the plug having a first diameter. Near its distal end, the plug tapers to a second, smaller diameter as shown. This smaller diameter distal end region may be useful to receive or otherwise accommodate portions of the capping member which might be folded back over the plug member when device 120 is loaded into a delivery sheath, potentially allowing use of a reduced diameter delivery sheath. Such recesses or other similar spaces for receiving or otherwise accommodating at least part of a capping member residing along a plug member portion will be recognized by those skilled in the art, and therefore, are encompassed by the present invention. Device 120 additionally includes a thin cover 133, which is somewhat snugly positioned over plug member 122. Cover 133 can be formed with any suitable material (e.g., a synthetic polymer), and may be useful to protect the device during product storage, handling and/or delivery. Device 120 may be sterilized before and/or after placement in cover 133. In one mode of delivery, device 120 is transferred directly from cover 133 and into an emplaced catheter or other similar delivery device so that the plug body 122 does not have to be directly touched by the physician during deployment.

Delivery devices useful in certain aspects of the present invention have a lumen communicating with a distal, open end. This "leading" distal end is configured to pass into passageways and other open spaces in the body. Although not necessary to broader aspects of the invention, this distal end, or any portion thereof, may be particularly configured to enhance travel of the device through certain body passageways, for example, including a tapered portion and/or having a dome-shaped or otherwise rounded tip. Accordingly, such devices can exhibit any suitable size, shape and configuration for performing the functions described herein, while avoiding substantially cutting or tearing surrounding soft tissues.

Where a delivery device is used to deliver a graft device into a fistula tract, such a device may have a length of about 2 inches to about 12 inches, more typically about 3 inches to about 9 inches, and even more typically about 4 to about 8 inches. Also, these devices may have an outside diameter of about 0.3 mm to about 3.2 mm, or about 0.5 to about 3.0 mm, or even about 1.0 mm to about 2.5 mm. In some preferred forms, the outside diameter of a delivery device will range from about 0.3 mm to about 10.0 mm, more typically from about 2.0 mm to about 7.0 mm.

In some embodiments, a delivery device is rigid or substantially rigid, and is configured to be generally straight, for example, for use in treating certain simple or straight fistulae. Alternatively, delivery devices useful in the invention can be configured to include one or more portions that are curvilinear, bent, or otherwise suitably shaped. In certain aspects, the distal end of a delivery device is curved to a degree to allow for easier passage of the distal end through a complex fistula, e.g., a horseshoe fistula, and/or through the primary fistula opening and into the alimentary canal. In some forms, a delivery device is composed of a malleable material such as but not limited to a woven or spirally-configured metal or alloy material, or a plastic (hydrocarbon-based) material, which may be bent to the necessary angle or curvature, for example, to allow passage through a fistula tract. The shape of such a delivery device may be adjusted at certain intervals of the procedure so as to allow the delivery device to pass further and further into the fistula tract, until the primary opening is identified. In some forms, the delivery device is generally straight in a relaxed condition but can flex to adapt to contours during passage.

In this regard, delivery devices, when used in the invention, can be formed with one or more of a variety of materials. A particular material may be selected to take advantage of one or more of its properties such as but not limited to its weight, durability, flexibility, etc. For example, a device may comprise a material having properties that allow the device to traverse a body passageway without buckling or kinking or causing unacceptable damage to soft tissues defining the passageway. Illustratively, the device, or selected portions thereof (e.g., the distal end), can exhibit a degree of flexibility. In this regard, a delivery device, or any portion thereof, may be rigid, malleable, semi-flexible, or flexible. In certain embodiments, an endoluminally advanceable device is particularly adapted for moving through and into body passages that angulate sharply or curve abruptly such as when traversing the alimentary canal, passing through and into a fistula opening, traversing a fistula tract, etc. In some of these embodiments, the device is configured to be directable or steerable through the passageway, and therefore, exhibits desirable characteristics, e.g., sufficient stiffness, to allow an operator to apply an adequate degree of ante-grade force to the device to allow it to traverse a passageway in a desirable manner.

Suitable materials for forming delivery devices or device components of the invention can include but are not limited to metallic materials including stainless steel, titanium, cobalt, tantalum, gold, platinum, nickel, iron, copper and the like, as well as alloys of these metals (e.g., cobalt alloys, such as Elgiloy®, a cobaltchromium-nickel alloy, MP35N, a nickel-cobalt-chromium-molybdenum alloy, and Nitinol®, a nickel-titanium alloy). Additionally or alternatively, the delivery device can include material in the form of yarns, fibers, and/or resins, e.g., monofilament yarns, high tenacity polyester, and the like. A delivery device can also include other plastic, resin, polymer, woven, and fabric surgical materials, other conventional synthetic surgical materials, such as a shape-memory plastic, and/or combinations of such materials. Further, appropriate ceramics can be used, including, without limitation, hydroxyapatite, alumina and pyrolytic carbon.

In some forms, a flexible delivery device will incorporate one or more adaptations for facilitating removal of the device from the body during a delivery procedure. Illustratively, a protective sleeve can incorporate scores, thinner portions, and other openings and non-openings that weaken a portion of the sleeve to facilitate a splitting operation in removing the sleeve from the tract. Such a weakened portion may include any suitable means for facilitating tearing or breaking along the area. In certain beneficial forms, a protective sleeve is controllably separable longitudinally into two or more pieces for removal, for example, as occurs in Peel-Away® catheters available from Cook Incorporated, Bloomington, Ind., USA. Such an apparatus with a separable sleeve is particularly useful in treating fistulae that have a secondary opening in the outer skin surface and a primary opening that is relatively difficult to access other than through the fistula tract, e.g. as occurs in a large percentage of enterocutaneous fistulae. In one aspect, a delivery system comprises a suitably sized and configured inner dilator, a splittable sheath, and a "pusher" device that is translatable through the sheath, wherein all of these can be received over an emplaced guidewire.

In some forms, an inventive device incorporates at least one object that can be X-ray, sonographically, or otherwise non-invasively visualized to determine its location in the body. Some inventive grafting devices, deployment systems, etc. are equipped with at least two imageable components such that the relative positioning of these components in the body can be verified during and/or after a procedure. These types of configurations are particularly useful in devices and systems having imageable components that can be caused or allowed to move relative to one another in the body such that the relative movement of the components can be tracked and verified during delivery, deployment, etc. Various device designs are contemplated in this regard. When a device or system includes multiple visualizable objects, any two of these objects may or may not be connected to one another. In some instances, a device is configured such that a particular arrangement of imageable components can be visualized from outside the body to indicate successful deployment, anchoring, function of the device, etc. Illustratively, when viewed from a particular vantage point outside the body, desirable positioning of two device components inside the body may be confirmed by measuring the distance between the two components as viewed from this vantage point. In other forms, two imageable components may be spaced from one another initially when viewed from a particular vantage point outside the body, and desirable positioning of the components inside the body may be confirmed by visualizing one component eclipsing the other component, for example, as viewed from this vantage point. Suitable markers and other imageable objects include those made from stainless steel, tantalum, platinum, gold, or other suitable materials. As well, substances containing tantalum, barium, iodine, or bismuth (e.g. in powder form) can be applied to inventive devices for imaging purposes.

With reference now to FIG. 5, shown is a capping member 150 according to another embodiment of the invention. Capping member 150 includes a generally octagonal, resilient support frame 151 embedded within a deformable covering material 152. An embedded frame arrangement of this sort can be provided in a variety of manners as described elsewhere herein, for example, by casting apolymerizable, crosslinkable or otherwise hardenable flowable material onto and around all or a portion of the frame member, and then causing the flowable material to polymerize, crosslink and/or otherwise harden. In one preferred embodiment, an embedded arrangement is provided by positioning a closed circumference wire frame between layers of a deformable material and then bonding the layers together to at least partially embed the frame in the material. In some cases, pieces of a somewhat flexible material are positioned around a frame, and then the material is physically, chemically and/or otherwise treated (e.g., lyophilized, heated, etc.) so that the material becomes less flexible and/or more uniform for maintaining the material in a desired configuration. In some forms, a Nitinol frame is positioned between layers of a polyurethane material such as THORALON® or a thermoplastic silicone, and then the layers are heated to thermoform the layers together around the frame. Yet, it will be understood that support frame 151 and covering material 152 can each be formed with a variety of materials as described elsewhere herein, and that the frame may be attached or otherwise associated with the covering material in other ways.

In this specific illustrative embodiment, capping member 150 additionally includes a washer 153 having a center hole 154. Washer 153 is positioned to the interior of support frame 151, and is also embedded within covering material 152 although the washer can be associated with the covering material in other non-embedded ways. Preferably but not necessarily, washer 153 is formed with a material such as stainless steel that can be non-invasively visualized, thus making both washer 153 and support frame 151 imageable in this way. While the relative dimensions of the various capping member components shown in FIG. 5 are advantageous in certain embodiments of the invention, it will be understood that these dimensions can be varied as desired to suit a particular application, patient, etc.

Covering material 152 may be desirably shaped (e.g., octagonally) and then combined with the support frame, or alternatively relatively large pieces of material may be utilized initially and then trimmed to a desired shape once combined with the frame. In an illustrative mode of formation, a Nitinol wire support frame and a stainless steel washer are positioned on a first, oversized sheet of polyurethane material. Thereafter, a second, oversized sheet of polyurethane material is placed over the first sheet in an overlapping relationship to sandwich the support frame and washer between the sheets. Any material layers used in this regard may be of the same or different thickness. The overlapping material layers are then pressed together (pressing optional) and thermoformed around the support frame and washer, thereby embedding these components between the thermoformed layers. Such a technique may be effective to substantially seal these components in the material. Thereafter, a center hole can be made in the covering material corresponding to the center hole 154 in the washer, and excess amounts of material can be trimmed from the periphery of the covering material. If present, excess material can be trimmed so that there is little or no material extending beyond the support frame. Alternatively, capping member 150 can be constructed such that covering material 152 includes a peripheral portion 155 extending a distance out and away from the support frame as shown.

In certain aspects of the invention, capping member 150 is combined with an elongate plug member to form a grafting device useful in the present invention. FIG. 6 shows a partial, side view of one illustrative inventive device 158 which includes a generally cylindrical, elongate plug member 160 extending from capping member 150. Support frame 151 and deformable covering material 152 are purposely not shown in FIG. 6 to more clearly show washer 153 and its relationship to elongate plug member 160 and other parts of the device. Plug member 160 has a distal end 161, and is configured to extend into and potentially fill a fistula tract. Its dimensions including its length can vary, with those skilled in the art recognizing suitable plug dimensions for a particular application. In some cases, a plug length is provided for extending through an entire fistula tract up to about 15 cm or longer, although such a plug could be cut to size as desired to fit all or a portion of a particular tract. As well, elongate plug member 160 can be formed with one or more of a variety of materials, and in some preferred embodiments, is formed with a rolled sheet-form material such as but not limited to a single- or multi-layered naturally-derived material (e.g., a collagenous ECM material). Illustratively, such a plug member may be formed as described elsewhere herein, for example, as described in regard to the plug member depicted in FIGS. 3A and 3B.

Capping member 150 and plug member 160 can be joined to one another in any suitable manner including some that involve bonding, suturing, coupling, mechanically fastening, etc. the two together. In some instances, the two are coupled to one another with an absorbable coupling device or material (e.g., an adhesive) to enable separation or uncoupling of the device components after a period of time following implantation, thus allowing the capping member to, for example, pass through and out of the bowel with naturally occurring fecal matter when certain fistulae are being treated. Such decoupling can be facilitated and/or promoted by naturally occurring forces generated during peristalsis. In certain forms, capping member 150 and plug member 160 will be coupled together at least in part by filament, thread, suture material, etc. In the specific illustrative embodiment depicted in FIG. 6, the two are held together with a system that includes a first, longitudinal pin 163 and a second, transverse pin 164. In a preferred embodiment, both of these pins are formed with PLGA or another absorbable material. In some forms, suture material is substituted for one or both pins to provide a retaining member. For example, transverse pin 164 can be replaced with 0 polydioxanone suture material that attaches to longitudinal pin 163 to keep it seated in the plug.

Continuing with FIG. 6, capping member 150 can be positioned atop plug member 160 such that washer 153 resides generally parallel to the plug's distal end 161. A central, longitudinal passage extends into plug 160 from its distal end. Washer 153 can be generally centered over the distal end of the plug so that the center hole 154 in the washer lines up with the opening to this longitudinal passage. A shank portion of longitudinal pin 163 can then be inserted through the hole in washer 153 and into the central, longitudinal passage in plug member 160. Longitudinal pin 163 has an enlarged head portion having a larger diameter than hole 154, thereby allowing pin 163 to securely hold capping member 150 atop plug member 160 when the pin is desirably anchored in the plug. A lateral passage extends at least partially through plug 160 near its distal end, and intersects with the longitudinal passage in the plug. A shank portion of lateral pin 164 can be inserted into this lateral passage and advanced until it desirably engages longitudinal pin 163. The two pins, in some instances, can be made to fit together (e.g., friction fit) or otherwise engage one another in a manner that desirably keeps the pins engaged to prevent longitudinal pin 163 from prematurely exiting plug 160.

Figure 8A:
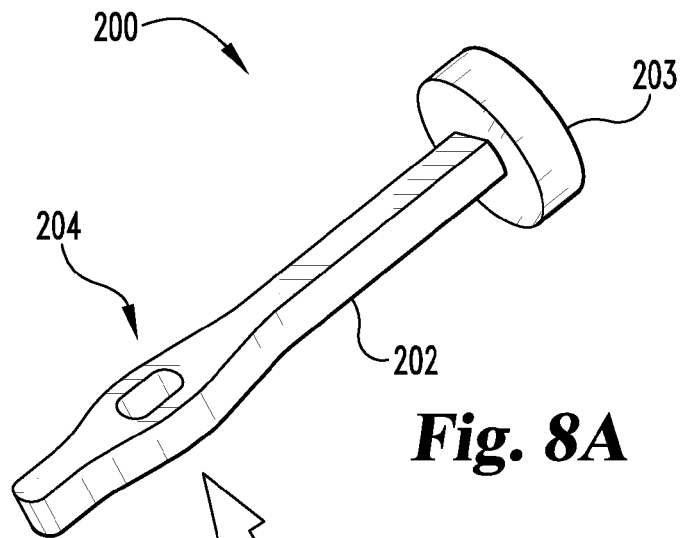
FIG. 8A shows a perspective view of a retaining system component of the invention.
Figure 8B:
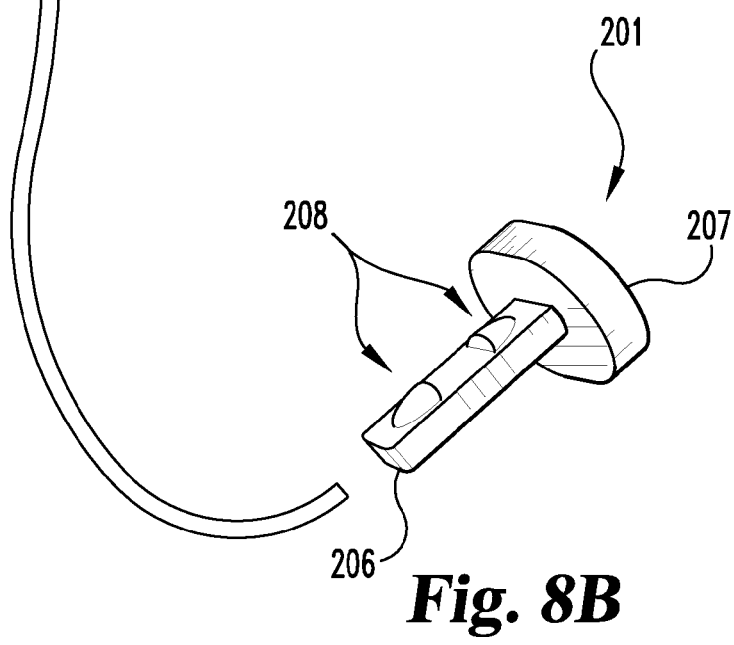
FIG. 8B shows a perspective view of another retaining system component of the invention.

FIGS. 8A and 8B show a retaining system according to one specific illustrative embodiment of the invention. This system can be employed as described above in relation to FIG. 6, and includes a longitudinal pin 200 and a lateral pin 201. Longitudinal pin 200 includes a shank portion 202 extending from an enlarged head portion 203. A passage 204 extends through shank portion 202 near the end of the shank opposite enlarged head portion 203. Lateral pin 201 includes a shank portion 206 extending from an enlarged head portion 207. Two protuberances 208 are positioned on each of opposite sides of shank portion 206. On each side, the two protuberance are spaced a distance from one another. When longitudinal pin 200 is positioned in a plug member as described above in relation to FIG. 6, the end of shank portion 206 opposite enlarged head portion 207 can be inserted into the lateral passage in the plug member and into passage 204 in the direction of the arrow shown. As shank portion 206 is advanced, portions of shank portion 202 adjacent passage 204 will contact the first, distal most protuberance on each side of shank portion 206. With sufficient force, shank portion 206 can be advanced until both distal protuberances pass entirely through passage 204 which, in some instances, may involve deformation of the protuberances. When both distal protuberances pass entirely through passage 204, the width of shank portion 202 will fit snugly in the space separating the two protuberances on each side of shank portion 206. Each protuberance will provide a wall inhibiting shank portion 206 from backing out of passage 204 and out of the plug. Also, shank portion 206 will prevent longitudinal pin 200 from backing out of the plug.

In addition to those shown, a variety of other alternatively shaped and configured protuberances, raised portions and other snap-fit type adaptations may be utilized in the invention. As well, these types of pins and other securing and retaining systems and their components can be formed with one or more of a variety of biocompatible materials including some that are resorbable and some that are nonresorbable. In one preferred embodiment, such devices are constructed with PLGA or another suitable resorbable material. Various other systems for attaching capping member 150 to plug member 160 will be recognized by the skilled artisan and therefore are encompassed by the present invention. These include various single- and multiple-part devices such as but not limited to those that deform to connect together, latch together, tie together, screw together, snap together, incorporate a detent mechanism, lock-fit together and variations and combinations thereof. Additionally, any of these elements may be radiopaque or otherwise incorporate a radiopaque material for visualization purposes as discussed elsewhere herein, for example, for comparing the positioning of one of these elements relative to a body part, other device component, delivery member, etc. In some modes of use, graft device 158 is implanted within a patient such that capping member 150 is positioned over a fistula opening 170 occurring in a bodily structure wall 171 (e.g., an intestinal wall), and elongate plug member 160 extends into a fistula tract 172 extending from this opening. In this position and referring now to FIG. 7, plug member 160 can be pulled in the direction of the arrow shown (i.e., away from the capped fistula opening) such that washer 153 and portions of deformable covering material 152 are drawn into the fistula tract as generally shown. Portions of deformable covering material including peripheral portion 155 remain outside the fistula tract. Peripheral portion 155 can, in some instances, promote and/or facilitate a better blockage or exclusion of the fistula tract from adjacent body lumens (e.g., the bowel lumen), and in some instances, will contribute to sealing off of a fistula opening.

Continuing with FIG. 7, longitudinal pin 163 and lateral pin 164 are purposely not shown in this illustration to more clearly show washer 153 and deformable covering material 152 and their relationship to the other device components and surrounding tissues. Graft device 158 may optionally incorporate a tether extending from elongate plug member 160 (e.g., away from the end opposite capping member 150), which may be useful in manipulating the position the device at certain points during delivery. A tether of this sort may be a suture (e.g., a 2-0 vicryl suture, 0-PDS suture, etc.) embedded within, attached to or otherwise associated with plug member 160.

Desirably, support frame 151 will be sized and configured so that it remains outside of the fistula tract (e.g., along the bodily structure wall in an area extending a suitable distance beyond the fistula opening) even when a considerable amount of pulling force is applied to plug member 160. In this manner, when capping member 150 is deformed as shown in FIG. 7, the support frame and an externally remaining portion 175 of the covering material will remain outside of the fistula tract, while washer 153 and an internalized covering material portion 176 will now reside within the fistula tract. Internalized covering material portion 176 includes material that previously (i.e., prior to deformation) resided outside of the fistula tract. In some forms, the capping member is made to deform so that portions of the covering material very snugly conform to patient tissue at the fistula opening in a generally non-planar condition such as a cupping or cup-like arrangement. As plug member 160 is pulled in the direction of the arrow, washer 153 moves away from support frame 151 in that same direction. Because support frame 151 and washer 153 are both formed with non-invasively imageable materials, when viewed from a vantage point corresponding to, for example, that shown in FIG. 7, it is possible to determine the relative positioning of the two components in the body as plug member 160 is pulled. This may be helpful, for example, to determine when a desired amount of deformation of the capping member has been achieved, for example, in an effort to try to seal off the fistula opening in instances where such sealing off can be achieved. When it can be visualized that the support frame and washer are desirably spaced or off-set from one another, the plug member 160 then can be secured in position, e.g., sutured to patient tissue using one or more sutures, to retain the conforming condition of the capping member. The desired amount of off-set can vary depending perhaps on the materials of construction of the grafting device, size of the fistula or other body passage being treated, etc.

Graft device 158 and other similar inventive devices are particularly suitable for treating enterocutaneous and other gastrointestinal fistulae, although such devices can be adapted to treat a variety of other fistula and non-fistula openings and other passages in the body. In some instances, these open spaces will occur naturally in the body, for example, as a native lumen or other open space in a bodily system, e.g., in an organ or other component of the circulatory, respiratory, digestive, urinary and reproductive, sensory, or endocrine systems. In certain aspects, an opening to be treated is one that exists naturally in the body but relates to a disease, defect, deformation, etc. Alternatively, an opening or passage to be treated may be one resulting from an intentional or unintentional trauma to the body including but not limited to some relating to vehicular accidents, gunshots and other similar wounds, etc., as well as some formed by passage of a medical instrument (e.g., a needle, trocar, etc.) through cutaneous, subcutaneous, and/or intracutaneous tissue. In preferred embodiments, assemblies of the invention can be used to plug or otherwise fill fistulae such as but not limited to urethro-vaginal fistulae, vesico-vaginal fistulae, tracheoesophageal fistulae, gastro-cutaneous fistulae, and any number of anorectal fistulae, such as recto-vaginal fistula, recto-vesical fistulae, recto-urethral fistulae, or recto-prostatic fistulae.

Inventive devices can be implanted in any suitable manner. In a preferred embodiment, graft device 158 is placed with the aid of a delivery sheath or other similar delivery device, for example, a splittable sheath as discussed elsewhere herein. In one mode of operation, the distal end of a wire guide is passed into an enterocutaneous fistula tract through a secondary fistula opening and toward a primary fistula opening under fluoroscopic guidance. The wire is advanced until its distal end enters the alimentary canal through the primary opening. Thereafter, the distal end of an over-the-wire dilator-sheath combination is advanced through the tract in a similar manner, for example, until the sheath is positioned at or just beyond the primary opening. The dilator is then removed, leaving the sheath (e.g., a check-flow sheath) and potentially also the guidewire in the tract. In some cases, the wire guide is removed with the dilator. Then, a suitably sized and shaped graft device such as graft device 158 is loaded into the sheath through its proximal end, for example, with the capping member 150 in a compressed condition (e.g., folded one or more times and/or rolled) entering the sheath first, and elongate plug member 160 following. The plug member may then be fully pushed into the sheath by hand. The capping member, in a compressed condition, is poised to return to its expanded condition upon being removed from the delivery device lumen.

Next, a pusher such as an over-the-wire pusher is introduced into the sheath proximal end and advanced toward the sheath distal end until at least a portion of the graft device is desirably pushed from the sheath distal end (e.g., with capping member 150 in an expanded condition and extending a distance into the alimentary canal). Then, the pusher can be placed in contact with the plug member 160 to provide back pressure, while the delivery sheath is removed, thus maintaining desirable positioning of the device inside the tract. After the sheath and pusher are removed, plug member 160 can be manipulated to achieve a desired deformation of capping member 150, for example, as described above. In some forms, it will be possible to grasp the plug body itself, for example, by hand or with a suitable instrument, for manipulation purposes. In other forms, the device will provide an extension (e.g., an attached suture) extending proximally from the plug body that can be grasped and manipulated. With capping member 150 desirably deformed (e.g., as verified by the imageable off-set distance between washer 153 and support frame 151), plug member 160 can then be secured in place (e.g., sutured or otherwise fixed to patient tissue at and/or around the secondary fistula opening) to maintain the capping member in this deformed condition. In some cases, the plug member will extend a distance out of the secondary opening when the capping member is deformed. This portion may optionally be trimmed off before or after the plug is secured in place.

In some preferred embodiments, care is taken to not block or otherwise close the secondary opening to facilitate drainage of the tract following the implantation procedure, for example, during remodeling when a remodelable material is utilized in the plugging assembly. Of course, it will be understood that the steps described above can occur in any suitable order as will be recognized by those skilled in the art. For example, while not necessary to broader aspects of the invention, a graft device may be preloaded into a delivery device before the delivery device is positioned in a fistula tract. Illustratively, a grafting device may be housed in a sheath (e.g., Flexor® sheath) for storage and/or transport. Such a sheath may be perforated which may be useful to hydrate and/or sterilize the grafting device prior to deployment. In some cases, when a delivery system component (e.g., a wire guide, dilator, pusher, etc.) is deemed not necessary for a particular delivery application, this component will be excluded from the delivery system and any associated methods of delivery.

In addition to graft device 158, the present invention provides a large variety of devices and systems in which it will be useful to employ multiple visualizable objects. Implantable medical devices in certain aspects of the invention include a first imageable component, a second imageable component and a device body that includes a deformable member that is deformable from a first condition to a second condition. Such a deformable member can be provided for anchoring, plugging, sealing, fixation, deployment, delivery and/or other purposes. The first imageable component and the second imageable component are arranged such that upon deformation of the deformable member from the first condition to the second condition, the position of the first imageable component relative to the second imageable component changes. Thus, in some embodiments, such a device is delivered to an implantation site in a patient. Thereafter, a deformable member (e.g., anchoring component) of the device is deformed from a first condition to a second condition such that the first imageable component changes position relative to the second imageable component. The change in position of the first imageable component relative to the second imageable component can then be visualized, for example, to indicate when the device has been desirably deployed. Devices in which it will be useful to incorporate multiple visualizable objects include, for example, those described in International Patent Application Serial No. PCT/US2007/061371, filed Jan. 31, 2007, and entitled "FISTULA GRAFTS AND RELATED METHODS AND SYSTEMS FOR TREATING FISTULAE" (Cook Biotech Incorporated), and U.S. Provisional Patent Application Ser. No. 60/947,573, filed Jul. 2, 2007, both of which are hereby incorporated by reference in its entirety.

In some forms, a fistula is drained prior to receiving a medical graft product of the invention therein. Such draining can be accomplished by inserting a narrow diameter rubber drain known as a seton through the fistula. The seton is passed through the fistula tract and tied as a loop around the contained tissue and left for several weeks or months, prior to definitive closure or sealing of the fistula. This procedure is usually performed to drain infection from the area, and to mature the fistula tract prior to a definitive closure procedure.

In one embodiment, a medical graft product of the invention includes a leader in association with the graft body, for example, a suture glued or tied to the graft body. This leader can be used to pull the graft body into a suitable position within a fistula. In some aspects, after the leader is used to sufficiently locate a suitable fistula graft within a patient, the string can be removed from the graft, for example, using cutting shears. In alternative forms, the string or suture can be made from a remodelable or otherwise absorbable material such that the string or suture can be left in place within the fistula tract. In these forms, the absorbable leader can be used to anchor or otherwise suitably secure the fistula graft within the implantation site. For example, the leader can be tied to patient tissue at a suitable location, for example, a location just inside or external to a secondary fistula opening. Further, in alternative embodiments, an illustrative fistula graft can be positioned so that it spans the entire length of a fistula tract, i.e., from the primary opening to a location at or external to a secondary opening. In these embodiments, the string or suture can be used to secure the tail of the graft to patient tissue at an external location.

Medical graft products of the invention can also be sealed within sterile medical packaging. For example, a medical graft product can have packaging including a backing layer and a front film layer. The medical graft product is sealed between the backing layer and the film layer utilizing a boundary of pressure-adhesive as is conventional in medical packaging. A cut-out may be provided in the backing layer to assist a user in separating the film layer from the backing layer.

Sterilization of a medical graft product may be achieved, for example, by irradiation, ethylene oxide gas, or any other suitable sterilization technique, and the materials and other properties of the medical packaging will be selected accordingly. Also, medical graft products of the invention can be contained in sterile packaging in any suitable state. Suitable states include, for example, a hydrated or dehydrated state. The medical graft products can be dehydrated by any means known in the art (e.g., lyophilization or air dried). If a medical graft product of the present invention is stored in a dehydrated state, it is preferred that it retains all of its biological and mechanical properties (e.g., shape, density, flexibility, etc.) upon rehydration.

The materials and other properties of the packaging will be selected accordingly. For example, the package can include indicia to communicate the contents of the package to a person and/or a machine, computer, or other electronic device. Such indicia may include the dimensions of, the type of materials used to form, and/or the physical state of, the contents of the package. In certain embodiments, a medical graft product is packaged for sale with instructions for use. For example, in a particularly preferred embodiment, a medical product includes at least one medical graft product sealed within a sterile package, wherein the packaging has visible indicia identifying the at least one medical graft product as having physical characteristics as described herein, and/or can contain or otherwise be associated with printed materials identifying the contents as having such physical characteristics and including information concerning its use as a medical graft product for treating fistulae. The packaging can also include visible indicia relating to the dimension of the at least medical graft product, and/or relating to the treatment site(s) for which the at least one medical graft product is configured.

The present invention also provides a line of medical products, wherein a medical product of the invention includes one or more medical graft products such as those described herein enclosed within a sealed package. When the medical product includes more than one medical graft product, for example, a plurality of medical graft products, the products can each be of substantially the same size and shape, or, alternatively, can vary with respect to size and shape.

Additionally, the medical graft products of the invention can be modified before, during, and/or after deployment. Illustratively, a product may be cut, trimmed, sterilized, and/or treated (e.g., brought into contact, impregnated, coated, etc.) with one or more desirable compositions, such as any of those previously disclosed herein, e.g., anticoagulants (e.g., heparin), growth factors or other desirable property modifiers. In certain aspects, following deployment of a graft body in accordance with the present invention, one or more portions of the body are trimmed off or otherwise removed, for example, material protruding from the primary opening and/or any secondary opening.

Further, the fistula treatment methods described herein can be used to close one or more fistula during a given medical procedure. Also, methods of the invention can be used to treat complex fistula. For multiple fistulae, multiple medical graft products can be engrafted until each of the fistula have been addressed. In cases of complex fistula, for example a horse-shoe fistula, there may be one primary opening and two or more fistula tracts extending from that opening. In such instances, a medical graft product may be configured with a graft body including one capping member and two or more elongate plug members. Each plug member can be drawn into the primary opening, and thereafter into one of the fistula tracts extending therefrom. Each of the elongate plug members and/or the capping member of the body can be secured by sutures and/or an adhesive, if necessary, and any excess material can be trimmed. Still further, while discussions herein have focused upon the treatment of fistulae, in certain embodiments, medical graft devices of the invention may be configured for and used in the treatment of other undesired voids or tracts through body tissues caused by trauma, disease or other causes, particularly such voids or tracts that originate at an organ wall or other tissue wall and extend into adjacent tissues.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. In addition, all patents and publications cited herein are indicative of the abilities of those of ordinary skill in the art and are hereby incorporated by reference in their entirety as if individually incorporated by reference and fully set forth.

What is claimed is:

1. A medical product useful for blocking an opening in a wall of a bodily structure in a body of a patient, the medical product comprising:

an implantable device that includes a deformable anchoring member positionable at the opening for placing a sheet-form covering over the opening, said implantable device also including a three-dimensional plug body that is formed separately from the sheet-form covering but attached to the sheet-form covering, the three-dimensional plug body comprised of a material receptive to tissue ingrowth, the implantable device being implantable with the sheet-form covering positioned over said opening and with the three-dimensional plug body extending from the sheet-form covering through the opening, wherein the deformable anchoring member includes a resilient wire support frame defining a central opening across which the sheet-form covering extends, the resilient wire support frame configured to extend around the opening in the wall of the bodily structure when the implantable device is implanted;

wherein the deformable anchoring member further includes a radiopaque component positioned in the central opening and discretely spaced from the resilient wire support frame;

wherein the radiopaque component has a first face having a width, a second face opposite the first face, and a thickness between the first face and second face, the thickness less than the width;

wherein the radiopaque component is connected to the resilient wire support frame by the sheet-form covering, the radiopaque component movable relative to the resilient wire support frame;

wherein said resilient wire support frame and said radiopaque component can be visualized under x-ray or sonography subsequent to implantation, and wherein the resilient wire support frame and said radiopaque component of said deformable anchoring member are arranged such that upon deformation of the deformable anchoring member from a first condition to a second condition, the position of the radiopaque component changes to the resilient wire support frame so that deformation of the deformable anchoring member can be visualized from outside of the body; and wherein said three-dimensional plug body has a length of about 1 to 8 inches.

2. The medical product of claim 1, wherein the resilient wire support frame is formed with Nitinol.

3. The medical product of claim 1, wherein the three-dimensional plug body comprises a synthetic polymeric material.

4. The medical product of claim 1, wherein the three-dimensional plug body comprises a collagen-containing material.

5. The medical product of claim 1, wherein the three-dimensional plug body comprises a remodelable material.

6. The medical product of claim 1, wherein the three-dimensional plug body comprises an extracellular matrix material.

7. The medical product of claim 6, wherein said extracellular matrix material comprises submucosa, serosa, pericardium, dura mater, peritoneum, or dermal collagen.

8. The medical product of claim 6, wherein said radiopaque component includes a metallic material.

9. The medical product of claim 1, wherein the sheet-form covering is positionable over said opening such that deforming the deformable anchoring member from the first condition to the second condition conforms the sheet-form covering to tissue at the opening so as to substantially seal off the opening.

10. The medical product of claim 1, wherein the sheet-form covering is positionable over said opening such that deforming the deformable anchoring member from the first condition to the second condition provides a convex surface of the sheet-form covering contacting tissue at said opening, the convex surface having a first portion residing externally of the opening and a second portion residing within the opening.

11. The medical product of claim 1, wherein the resilient wire support frame includes a closed circumference frame member lying within a single generally flat plane.

12. The medical product of claim 11, wherein the radiopaque component is positioned to the interior of said closed circumference frame member when the deformable anchoring member is in the first condition.

13. The medical product of claim 11, wherein the sheet-form covering material includes a synthetic polymeric layer extending between outer portions of said closed circumference frame member.

14. The medical product of claim 1, wherein the three-dimensional plug body is of sufficient size to generally fill the opening.

15. The medical product of claim 1, wherein the three-dimensional plug body comprises a resorbable material.

16. The medical product of claim 1, further comprising an actuating member connected to and extending from the deformable anchoring member, wherein the actuating member is configured to extend through the opening when the implantable device is implanted and is actuatable to convert the deformable anchoring member from the first condition to the second condition.

17. The medical product of claim 1, wherein said resilient wire support frame and said radiopaque component are configured for visualization under x-ray subsequent to delivery of the implantable device to the implantation site.

18. The medical product of claim 1, wherein said resilient wire support frame and said radiopaque component are spaced a distance from one another.

19. A method for blocking an opening in a wall of a bodily structure, comprising:

providing an implantable medical device that includes a deformable anchoring member positionable at the opening for placing a sheet-form covering over the opening, said implantable medical device also including a three-dimensional plug body that is formed separately from the sheet-form covering but attached to the sheet-form covering, the three-dimensional plug body comprised of a material receptive to tissue ingrowth, the implantable device being implantable with the sheet-form covering positioned over said opening and with the three-dimensional plug body extending from the sheet-form covering through the opening, wherein the deformable anchoring member includes a resilient wire support frame defining a central opening across which the sheet-form covering extends, the resilient wire support frame configured to extend around the opening in the wall of the bodily structure when the implantable device is implanted;

wherein the deformable anchoring member further includes a radiopaque component positioned in the central opening and discretely spaced from the resilient wire support frame;

wherein the radiopaque component has a first face having a width, a second face opposite the first face, and a thickness between the first face and second face, the thickness less than the width;

wherein the radiopaque component is connected to the resilient wire support frame by the sheet-form covering, the radiopaque component movable relative to the resilient wire support frame;

wherein said resilient wire support frame and said radiopaque component can be visualized under x-ray or sonography subsequent to implantation, and wherein the resilient wire support frame and said radiopaque component of said deformable anchoring member are arranged such that upon deformation of the deformable anchoring member from a first condition to a second condition, the position of the radiopaque component changes relative to the resilient wire support frame so that deformation of the deformable anchoring member can be visualized from outside of the body; and wherein said three-dimensional plug body has a length of about 1 to 8 inches;

delivering the implantable medical device to an implantation site which includes said opening so that the sheet-form covering is positioned over said opening and the three-dimensional plug body extends from the sheet-form covering through the opening;

deforming the deformable anchoring member from the first condition to the second condition, wherein the radiopaque component changes position relative to the resilient wire frame; and visualizing the change in position of the radiopaque component relative to the resilient wire support frame.

* * * * *